United States Patent [19]
Serre et al.

[11] Patent Number: 5,888,833
[45] Date of Patent: Mar. 30, 1999

[54] ANTIGENS RECOGNIZED BY ANTIBODIES TO RHEUMATOID ARTHRITIS, THEIR PREPARATION AND THEIR APPLICATIONS

[75] Inventors: Guy Serre, Toulouse; Gérard Somme, Bures Sur Yvette; Christian Vincent, Lauzerville, all of France

[73] Assignee: Biomerieux S.A., Marcy L'Etoile, France

[21] Appl. No.: 253,762

[22] Filed: Jun. 3, 1994

Related U.S. Application Data

[63] Continuation of Ser. No. 958,353, Jan. 27, 1993, abandoned.

[30] Foreign Application Priority Data

| Apr. 26, 1991 | [FR] | France | 91 04983 |
| Sep. 24, 1991 | [FR] | France | 91 11727 |
| Apr. 24, 1992 | [WO] | WIPO | PCT/FR92/00371 |

[51] Int. Cl.$^6$ ............................. C07K 1/00; C07K 14/00; G01N 33/564; G01N 33/561
[52] U.S. Cl. .................... 436/509; 436/506; 436/516; 530/350; 530/403
[58] Field of Search ..................... 436/506, 516; 530/350, 403

[56] References Cited

FOREIGN PATENT DOCUMENTS

| 175310 | 3/1986 | European Pat. Off. . |
| 37 21 790 | 1/1989 | Germany . |
| WO 89/07764 | 8/1989 | WIPO . |

OTHER PUBLICATIONS

Huet et al, Ann Rheum Dis SO(9): 611–618, 1991.
Dale et al., "Characterization of Two Monoclonal Antibodies to Human Epidermal Keratohyalin: Reactivity with Filaggrin and Related Proteins", *The Journal of Investigative Dermatology*, vol. 88, No. 3, Mar. 1987, pp. 306–313.
Lonsdale-Eccles et al., "High–Molecular–Weight Precursor of Epidermal Filaggrin and Hypothesis for its Tandem Repeating Structure", *Biochemistry*, vol. 23, No. 6, 1984, pp. 1239–1245.
*Chemical Abstracts*, vol. 103, No. 25, Dec. 23, 1985, p. 605, Abstract No. 211908: Fleckman et al., "Profilaggrin, a high–molecular–weight precursor of filaggrin in human epidermis and cultured keratinocytes" (*J. Invest. Dermatol.*, 1985, 85(6), 507–12).
Hoet et al., "The Perinuclear Factor, a Rheumatoid Arthritis–Specific Autoantigen, is Not Present in Keratohyalin Granules of Cultured Buccal Mucosa Cells", *Clinical and Experimental Immunology*, vol. 84, No. 1, Apr. 1991, pp. 59–65.
Meek et al., "Epidermal Filaggrin is Synthesized on a Large Messenger Ribonucleic Acid as a High–Molecular–Weight Precursor", *Biochemistry*, vol. 22, No. 21, Oct. 11, 1983, pp. 4867–4871.
Serre et al., "Anticorps Anti–Stratum Corneum D'Oesophage De Rat, Auto–Anticorps Anti–Keratines Epidermiques Et Anti–Epiderme Dans La Polyarthrite Rhumatoide Et Differentes Affections Rhumatologiques", *Revue Du Rhumatisme*, vol. 53, No. 11, 1986, pp. 607–614.
Harding et al., "Histidine–rich Proteins (Filaggrins): Structural and Functional Heterogeneity during Epidermal Differentiation", *Journal of Molecular Biology*, vol. 170, No. 3, Nov. 1983, pp. 651–673.

*Primary Examiner*—James C. Housel
*Assistant Examiner*—V. Ryan
*Attorney, Agent, or Firm*—Bell Seltzer; Intellectual Property Law Group of Alston & Bird LLP

[57] ABSTRACT

The present invention relates to antigens extracted from mammalian malpighian epithelia, in particular rat esophageal epithelium or human epidermis, which are specifically recognized by the autoantibodies present in patients suffering form rheumatoid arthritis in respect of antigenic determinants in common with filaggrin and human profilaggrin, as well as to the antigenic proteins of which said antigens are composed and to the peptide fragments derived therefrom. The invention relates to the use of these antigens, proteins and peptide fragments, and that of filaggrin and human profilaggrin, for the preparation of antigenic compositions, and to their applications, in particular for the diagnosis of rheumatoid arthritis. The invention also relates to the preparation of antibodies directed towards these antigens, and to their applications.

2 Claims, 11 Drawing Sheets

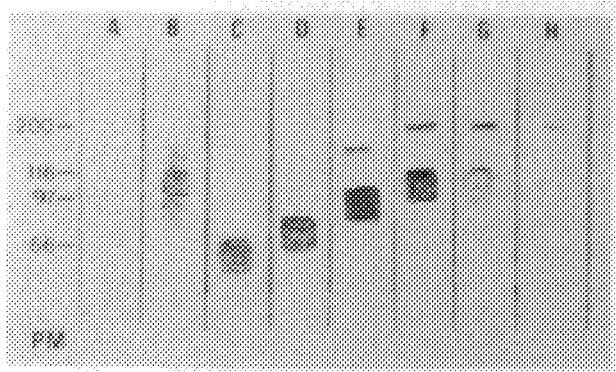
FIG. 5A.
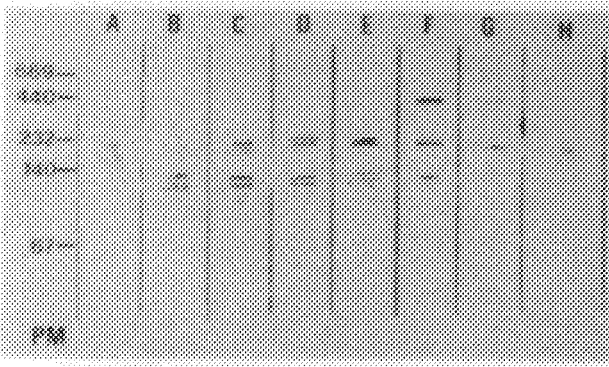
FIG. 5B.
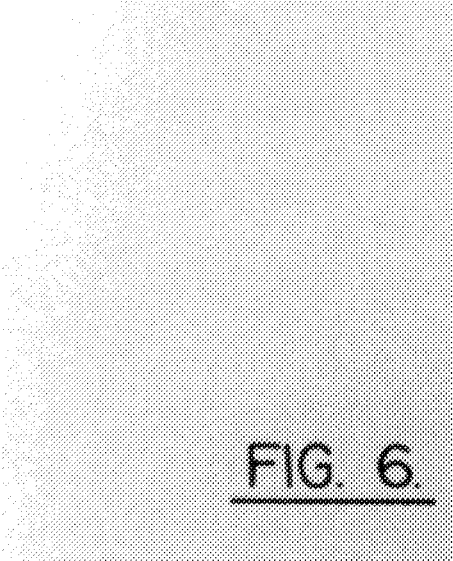
FIG. 6.
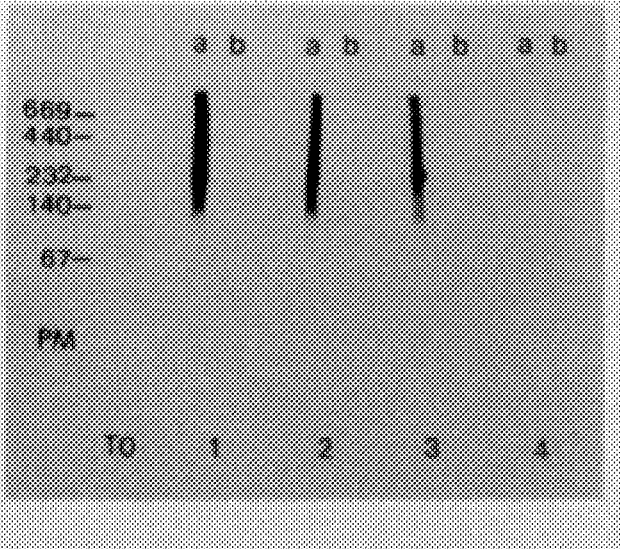

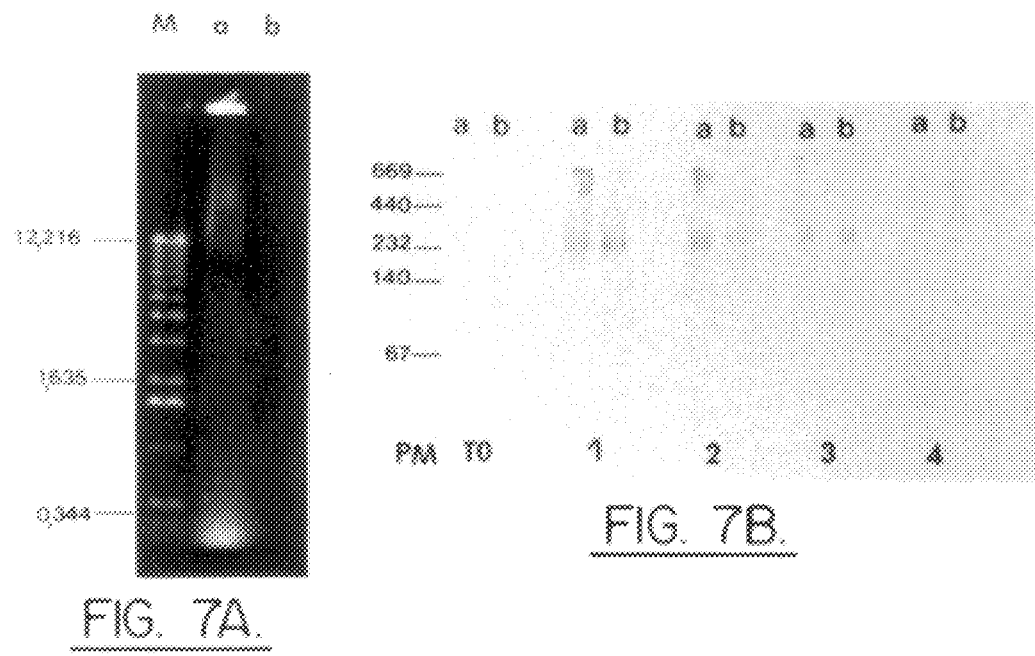
FIG. 7A.
FIG. 7B.
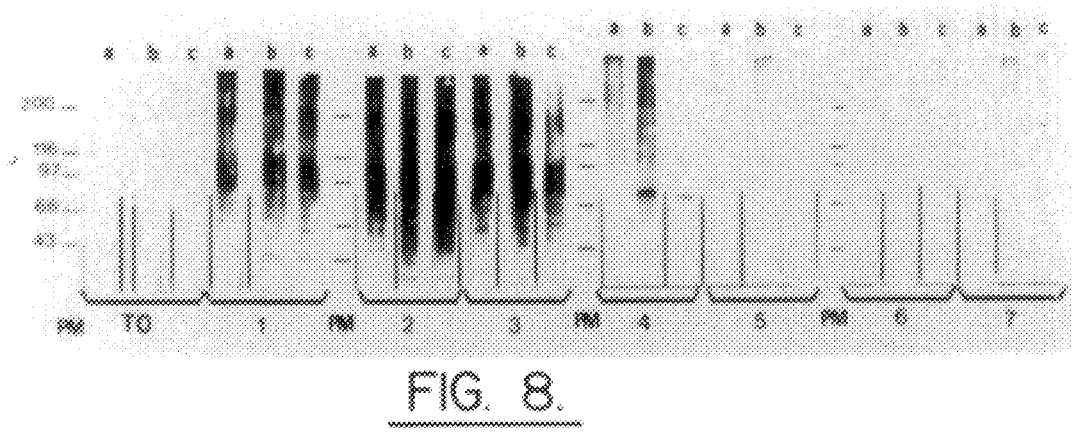
FIG. 8.

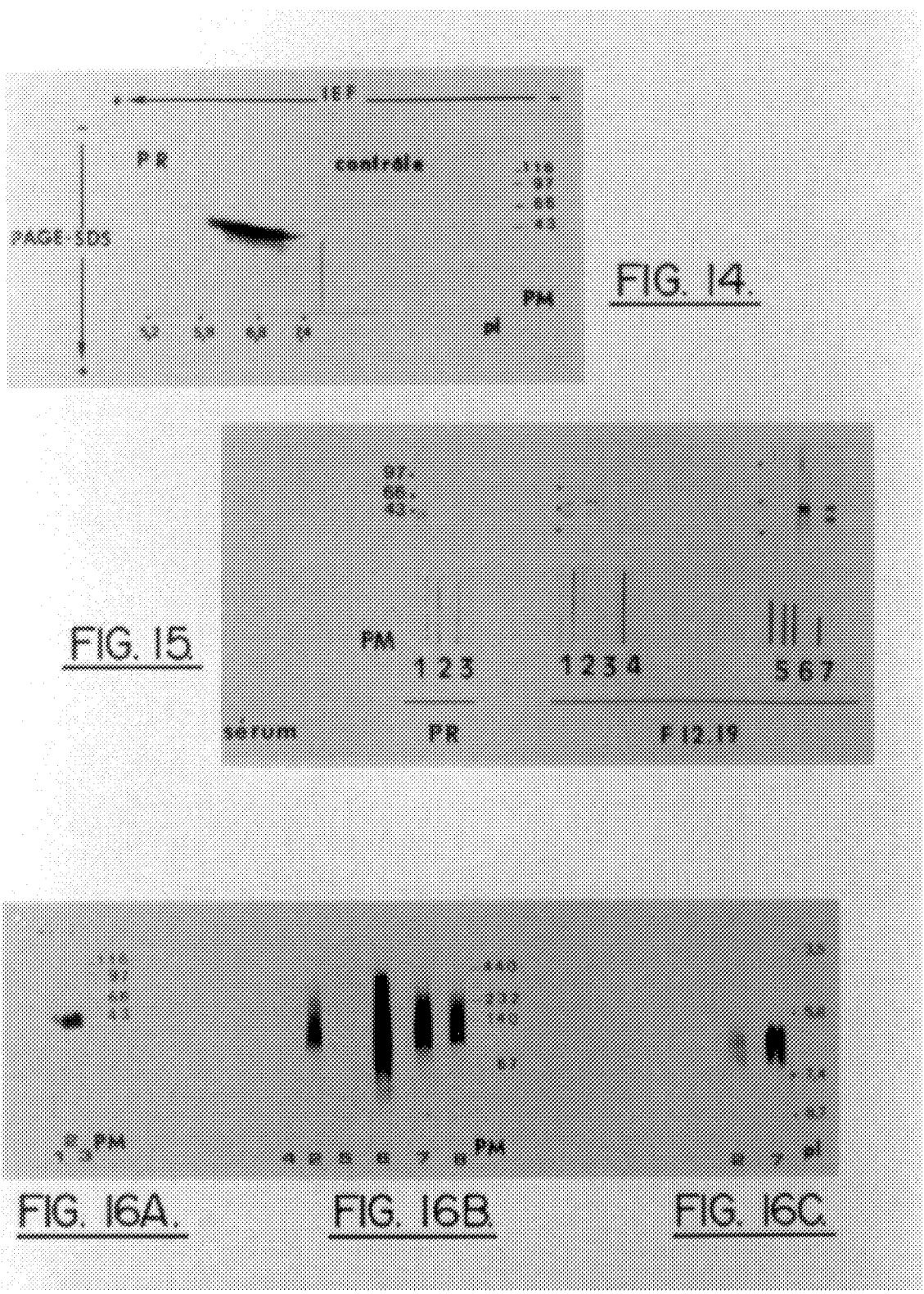

ANTIGENS RECOGNIZED BY ANTIBODIES TO RHEUMATOID ARTHRITIS, THEIR PREPARATION AND THEIR APPLICATIONS

This application is a continuation of application Ser. No. 07/958,353, filed Jan. 27, 1993 now abandoned.

FIELD OF THE INVENTION

The present invention relates to the use of human filaggrin and antigens related thereto for the diagnosis or treatment of rheumatoid arthritis (RA).

BACKGROUND OF THE INVENTION

RA is the most common chronic inflammatory rheumatic disease. It affects approximately 2% of the population of developed countries.

RA is progressive and incapacitating, and creates difficult diagnostic problems in its early forms while at the same time calling for specific treatment. Apart from clinical and radiological signs, the rheumatologist currently has at his disposal only rather non-specific biological tests for his diagnosis. The most widely used of these are the Rose-Waaler test and the latex test, which detect rheumatoid factor in 7 cases of RA out of 10. However, the specificity of these tests is very poor, since these factors are detected in most other autoimmune pathologies and even in some healthy individuals.

The presence of autoantibodies directed towards cellular components is the general feature of autoimmune diseases such as RA, systemic lupus erythematosus, scleroderma or polymyositis. Among the many types of autoantibodies identified in these diseases, those specifically present in patients suffering from RA and reacting with an esophageal epithelial antigen were described for the first time by B. J. J. Young et al. in Br. Med. J. 2:97–99, (1979). These autoantibodies were named at the time "antikeratin antibodies". Hitherto, it was commonly accepted that they were directed towards cytokeratins.

These autoantibodies specific to RA are at the present time detected and titrated by indirect immuno-fluorescence (IIF) on transverse cryosections of rat esophagus.

IIF techniques possess, however, drawbacks which limit their use for the routine diagnosis of RA. In particular, they necessitate the use of tissue cryosections, which involves a loss of time and the participation of specialized personnel; in particular, analysis and reliable interpretation of the results can be carried out only by individuals familiar with histology.

It is hence especially desirable to have available purified preparations of the antigens recognized by the autoantibodies specific to RA, and which may be used in standard techniques of immunochemical diagnosis.

G. Serre et al. in Rev. Rhum. 53(11):607–614 (1986) have shown that an antigen defined by these autoantibodies is characteristic of certain cornified malpighian epithelia of mammals. Present chiefly in the stratum corneum of these epithelia, it is expressed, for example, in the human epidermis.

However, hitherto, no success was achieved either in identifying such an antigen precisely, or in purifying it.

BRIEF DESCRIPTION OF THE DRAWINGS

FIG. 5A shows the modelling, obtained after SDS PAGE, of immunoreactivity profiles of the antigenic fractions purified by sequential gel filtration/hydrophobic interaction chromatography, where differences in intensity of immunoreactive bands or regions reflect the relative abundance of antigenic proteins in each fraction (A–H).

FIG. 5B shows the modelling, obtained after SDS PAGE under native conditions, of the immunoreactivity profiles of the antigenic fractions purified by sequential gel filtration/hydrophobic interaction chromatography, where the differences in intensity of the immunoreactive bands or regions reflect the relative abundance of antigenic proteins in each fraction (A–H).

FIG. 6 shows the immunotransfer analysis of the proteins in an antigenic extract which is either digested (lanes "a") or not digested (lanes "b") with proteinase K, separated by PAGE under native conditions, and immunodetected with GIFRE+ sera from patients with rheumatoid arthritis (lanes 1–3) and GIFRE− sera from one patient with rheumatoid arthritis (lane 4); $C_o$ is a negative control.

FIG. 7A shows the analysis of an extract of rat esophageal epithelium treated (lane b) or not treated (lane a) with micrococcal nuclease, and then analyzed by electrophoresis in a 1% agarose gel, where M indicates size markers in kilobase pairs.

FIG. 7B shows the immunotransfer analysis after PAGE under native conditions carried out with three GIFRE+ sera from patients with rheumatoid arthritis (lanes 1–3) and GIFRE− sera from one patient with rheumatoid arthritis (lane 4); $C_o$ is a negative control.

FIG. 8 shows the immunodetection of an extract of rat esophageal epithelium which was separated by SDS-PAGE and incubated with periodic acid, and reacted with GIFRE+ sera from three patients with rheumatoid arthritis (lanes 1–3) and GIFRE− sera from two patients with rheumatoid arthritis (lanes 4–5), and two control sera (lanes 6–7).

FIG. 14 shows the analysis of the proteins in the NP40 extract of mammary epidermis which were precipitated with ethanol, and separated by two-dimensional IEF/SDS-PAGE gel. Immunodetection was carried out using serum from a patient with rheumatoid arthritis (RA) and a control serum.

FIG. 15 shows an NP40 extract of mammary epidermis immunodetected with serum of a patient with rheumatoid arthritis (Panel A); urea-soluble cytokeratins immunodetected with the anticytokeratin monoclonal antibody F12–19(Panel B); and proteins in epidermal extract (lane 5), a fraction enriched with cytokeratins (lane 6), and the pure urea-soluble cytokeratins (lane 7) immunodetected with the anticytokeratin monoclonal antibody F12–19.

FIG. 16A shows the analysis of the proteins in an extract of mammary epidermis separated in SDS-PAGE and immunodetected with sera from patients with rheumatoid arthritis (lanes 1 and 3) and the antifilaggrin MAb AKH-1 (lane 2).

FIG. 16B shows the analysis of the proteins in an extract of mammary epidermis separated by PAGE under native conditions and immunodetected with the antifilaggrin MAb AKH-1 (lane 2), a control MAb (lane 4), control serum (lane 5), and sera from patients with rheumatoid arthritis (lanes 6–8).

FIG. 16C shows the analysis of the proteins in an extract of mammary epidermis separated by IEF (pHi 3 to 9) and immunodetected with the antifilaggrin MAb AKH-1 (lane 2), and serum from a patient with rheumatoid arthritis (lane 7).

DETAILED DESCRIPTION OF THE INVENTION

Figure 1:
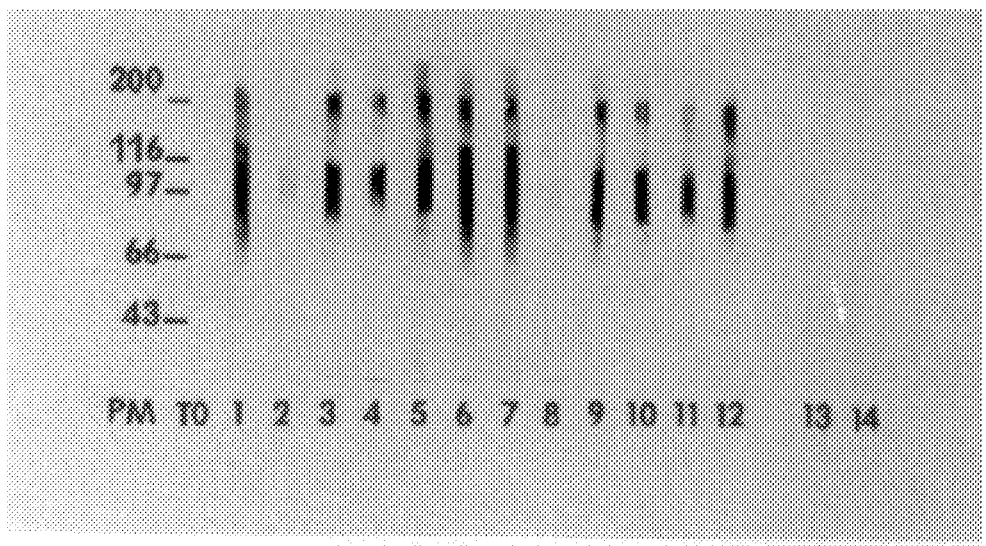
FIG. 1 shows the immunotransfer analysis of an extract of rat esophageal epithelium separated by SDS-PAGE.

The work carried out by the Inventors in the field of epidermal and malpighian differentiation, in particular the production of monoclonal antibodies for the definition of new differentiation antigens and the study of human autoantibodies to these same antigens, has enabled them to show that the anti-stratum corneum antibodies of rat esophagus are authentic autoantibodies, which do not recognize cytokeratins but other antigens expressed, in particular, in murine esophageal epithelium and human epidermis.

More exhaustive work has now enabled the Inventors to extract from rat esophageal epithelium and from human epidermis antigens bearing antigenic determinants specifically recognized by the autoantibodies present in patients suffering from RA, to purify these antigens and to characterize them biochemically.

The subject of the present invention is preparations of antigens possessing the following properties:
- they are capable of being extracted from human epidermis or from rat esophageal epithelium,
- they are protein in nature,
- treatment with a nuclease does not modify their immunoreactivity,
- treatment with ethanol does not modify their immunoreactivity,
- treatment with trichloroacetic acid (TCA) does not modify their immunoreactivity,
- they are water-soluble,
- they are specifically recognized by the autoantibodies present in patients suffering from RA.

A first antigen specifically recognized by the autoantibodies present in patients suffering from RA was extracted from human epidermis.

This antigen is characterized more especially by the following properties:
- after polyacrylamide gel electrophoresis (PAGE) under native conditions, it separates into several antigenic proteins which migrate like reference standards (which are globular proteins) whose molecular weights are between 80 and 400 kD approximately, the most immunoreactive proteins being located in regions lying between approximately 80 and 120 kD;
- after isoelectric focusing (IEF), it dissociates into several antigenic proteins whose isoelectric points (pHi) vary from 5.8 to 7.4;

after two-dimensional electrophoresis of the IEF type followed by migration in PAGE in the presence of sodium dodecyl sulfate (SDS), it appears as an antigenic protein of average apparent molecular weight approximately 40 kD whose pHi varies from 5.8 to 7.4.

The Inventors have also found that this antigen possesses immunological and biochemical properties in common with human filaggrin, and corresponds to a proteolytic fragment of profilaggrin (the latter being the precursor of filaggrin).

Following this finding, the Inventors carried out a test on the immunoreactivity of filaggrin and of human profilaggrin with autoantibodies specific to RA, and demonstrated a reactivity similar to that of the antigen according to the invention described above.

Filaggrin is a family of proteins which has been identified in various species in keratinizing epithelia. They are histidine-rich, basic proteins. They are derived from the dephosphorylation and proteolysis of a precursor, profilaggrin, and then undergo a maturation during which the basic arginine residues are converted to neutral citrulline residues. This maturation phenomenon is partially responsible for the lack of homogeneity of filaggrin preparations which, for the same molecular weight, take the form of several isoelectric variants.

The precursor of filaggrin, profilaggrin, consists essentially of repeated domains of filaggrin; this results in a close immunological relationship between these two molecules [for a review on filaggrins, see DALE et al. Cellular and Molecular Biology of Intermediates Filaments, pp. 393–412, GOLDMAN and STEIWERT eds. Plenum Press (1990)].

Profilaggrin and filaggrin are extracted from epidermis by the action of buffers of high ionic strength and in the presence of urea. However, filaggrin, when purified, is partially soluble in buffers of low ionic strength, at neutral pH.

No similarity between human filaggrin and an antigen recognized by the class G anti-stratum corneum autoantibodies, termed "antikeratins", specific to RA had been suggested hitherto. The only relationship which could be established by a few authors is the observation of a colocalization between filaggrin or profilaggrin and perinuclear factor (which is an immunochemical marker of rheumatoid arthritis). These authors, however, came to the conclusion that perinuclear factor is different from filaggrin [HOET et al. Clin. Exp. Immunol. 84. 59–65 (1991)].

The Inventors also extracted from rat esophageal epithelium a second antigen specifically recognized by the autoantibodies present in patients suffering from RA.

This antigen possesses the following properties:
after SDS-PAGE electrophoresis, it separates into the following two antigenic proteins:
a first protein of apparent average molecular weight approximately 210 kD,
a second protein of apparent average molecular weight between approximately 90 and 130 kD,
after PAGE electrophoresis under native conditions, it separates into the following three antigenic proteins:
a first protein which migrates like horse spleen ferritin (molecular weight: 440 kD),
a second protein which migrates like ox liver catalase (molecular weight: 232 kD),
a third protein which migrates between ox heart lactic dehydrogenase and bovine serum albumin (respective molecular weights: 140 kD and 67 kD),
after two-dimensional electrophoresis of the IEF type followed by migration in SDS-PAGE, it dissociates into three antigenic proteins:
a first protein of apparent average molecular weight approximately 210 kD whose pHi values vary from approximately 5.85 to 6.85,
a second protein of apparent average molecular weight between approximately 90 and 130 kD whose pHi values vary from approximately 5.85 to 7.35,
a third protein whose apparent average molecular weight varies from approximately 120 to 67 kD while its pHi varies from approximately 5 to 7.5,
after sequential gel filtration chromatography and hydrophobic interaction chromatography and then SDS-PAGE analysis, this antigen separates into two antigenic protein fractions of different relative hydrophobicity:
the more hydrophobic fraction contains the protein of apparent average molecular weight approximately 210 kD and the protein of apparent average molecular weight between approximately 90 and 130 kD,
the less hydrophobic fraction contains the protein of apparent average molecular weight between approximately 120 and 67 kD.

The Inventors, in addition, made the following observations:

The antigen of rat esophagus exhibits immunological cross-reactions with human filaggrin (and naturally profilaggrin) and filaggrin extracted from rat epidermis, but these cross-reactions do not appear to involve the same epitopes. In effect, filaggrin extracted from rat epidermis is not recognized by the autoantibodies specific to RA; the implication is that the epitopes recognized by these autoantibodies are not the ones which participate in the cross-reactions between the antigen of rat esophageal epithelium and rat epidermal filaggrin. The situation is quite different in the case of the cross-reactions, between rat esophageal epithelial antigen and human filaggrin, which involve at least a part of the epitopes recognized by the autoantibodies specific to RA. It should also be noted that the epitopes involved in these cross-reactions, and recognized by the autoantibodies specific to RA, represent only a part of the epitopes of human filaggrin. For example, the monoclonal antibody AKH1 [DALE et al. J. Invest. Dermatol 88, 306–313 (1987)] which recognizes an epitope of human filaggrin does not recognize the antigen of rat esophageal epithelium; moreover, when the antibody AKH1 is used in indirect immunofluorescence on cryosections of human epidermis, the labeling observed is different from that obtained when anti-stratum corneum autoantibodies specific to RA are used.

Human epidermal antigen, for its part, exhibits cross-reactions with filaggrin and human profilaggrin in which epitopes recognized by the autoantibodies specific to RA, and also other epitopes such as that recognized by the monoclonal antibody AKH1, participate.

All the protein fractions described above, of which the antigens of human epidermis and of rat esophagus are composed, have been purified and tested with the autoantibodies present in patients suffering from RA. These protein fractions are seen to possess individually immunological properties equivalent to those of the antigens from which they are derived.

The invention also encompasses fractions of the antigens of human epidermis and of rat esophagus and peptide fragments derived from these antigens and from the fractions thereof, as well as the peptide fragments derived from filaggrin and from human profilaggrin or from the fractions thereof and bearing epitopes recognized specifically by the autoantibodies specific to RA.

In the sense used in the present invention, fraction is understood to mean any antigenic preparation recognized by anti-stratum corneum autoantibodies specific to RA and obtained from one of the antigens mentioned above by a suitable fractionation technique (electrophoresis, chromatography, electric focusing, and the like). This encompasses the fractions obtained from preparations of filaggrin and of human profilaggrin, as well as the fractions described more specifically above, obtained from the water-soluble antigens of human epidermis and of rat esophagus epithelial cells.

The invention consequently also relates to the three proteins demonstrated after two-dimensional electrophoresis of the IEF type, followed by migration in SDS-PAGE, of the antigen extracted from rat esophageal epithelium.

These three proteins were also demonstrated in the protein fractions obtained after sequential gel filtration and hydrophobic interaction chromatography of the antigen extracted from rat esophageal epithelium and then electrophoresis under denaturing conditions.

The first of these three proteins possesses an apparent average molecular weight of approximately 210 kD and pHi values varying from approximately 5.85 to 6.85; the second possesses an apparent molecular weight of between 90 and 130 kD and pHi values varying from approximately 5.85 to 7.35; and the third possesses an apparent average molecular weight of between 67 and 120 kD and pHi values varying from approximately 5 to 7.5.

The invention also relates to the protein demonstrated after two-dimensional electrophoresis of the IEF type, followed by migration in SDS-PAGE, of the antigen extracted from human epidermis. This protein has a molecular weight of approximately 40 kD and pHi values varying from approximately 5.8 to 7.4.

In the sense used in the present invention, peptide fragments are understood to mean:
- the peptide fragments resulting from the proteolysis of antigenic proteins caused, for example, by the action of proteases such as trypsin, chymotrypsin, papain, protease V8, and the like, and proteolytic fragments extracted from tissues and resulting from the natural maturation of antigenic proteins;
- antigenic peptides of at least 5 amino acids obtained from the sequence of one of the antigens mentioned above; this encompasses, in particular, synthetic peptides, as well as peptides obtained by genetic engineering, which reproduce the sequence of an antigen fragment bearing an epitope recognized by the anti-RA autoantibodies.

Irrespective of the method for obtaining these antigenic peptides, those which bear the desired epitope or epitopes will be selected, on the basis of their reactivity with the autoantibodies specific to RA.

Such peptides can, for example, be obtained from fragments of the sequence of human profilaggrin, which is known [see, for example, the publication of GAN et al., Biochem. 29, 9432–9440 (1990)].

The invention also relates to preparations of antigens, characterized in that the latter are recognized by autoantibodies specific to RA and exhibit immunological cross-reactions, involving antigenic determinants recognized by said autoantibodies, with an antigen (protein, protein fraction, peptide fragment) according to the invention and/or with human profilaggrin or filaggrin.

These antigens can, in particular, be obtained from malpighian epithelia and, where appropriate, from articular tissues of mammals (including those of species other than man and rat), as well as from cultures of the cells of which these tissues are composed.

The work of the Inventors hence leads to the production of a series of new soluble antigens recognized specifically by class G autoantibodies specific to RA, and to the demonstration of a specific reaction of said autoantibodies with human filaggrin.

This work finds direct application in the diagnosis of RA. Consequently, the invention also relates to:
- antigenic compositions for diagnosis of the presence of autoantibodies in a biological sample of a patient suffering from RA, which compositions are characterized in that they contain at least one antigen selected from the group consisting of: the antigen extracted from rat esophagus epithelial cells; the antigen extracted from human epidermis; the fractions thereof or the peptide fragments thereof, as defined above;
- the use of filaggrin, profilaggrin, the fractions thereof or the peptide fragments thereof for the in vitro diagnosis of RA, in particular for the preparation of antigenic compositions for diagnosis of the presence of autoantibodies in a biological sample of a patient suffering from RA.

These compositions permit the formation of an antigen-antibody complex between the antigens of the invention (proteins, protein fractions and peptide fragments) and the autoantibodies present in a biological sample, such as the serum of a subject suffering from RA.

The subject of the present invention is a method for detecting the class G autoantibodies specific to RA in a biological fluid, which method is characterized in that it comprises at least one step during which said biological fluid is brought into contact with at least one antigen selected from the group consisting of:
- human filaggrin, human profilaggrin;
- an antigen extracted from rat esophagus epithelial cells, as defined above;
- an antigen extracted from human epidermis, as defined above;
- the fractions or peptide fragments derived from the above antigens;

wherein the fluid and the antigen(s) are brought into contact under conditions that permit the formation of an antigen-antibody complex with the autoantibodies specific to RA which may be present.

The antigen is, where appropriate, labeled or conjugated to a carrier molecule.

Following this step, detection in the biological fluid of the immunological complex formed is carried out by physical or chemical methods known per se.

The above diagnostic method may be carried out by means of an outfit or kit comprising:
- at least one antigen (proteins, fractions and fragments) according to the invention, where appropriate labeled, or a conjugate of this antigen or protein with a carrier molecule;
- reagents to make up a medium suited to the immunological reaction with the autoantibodies which may be present in a biological sample;
- one or more reagents for detection of the immunological complex formed;
- if necessary, reference samples such as one or more negative serum/sera and one or more positive serum/sera.

According to a preferred embodiment of the method according to the invention, an immunotransfer test for detection of the class G anti-stratum corneum autoantibodies specific to RA was developed.

An immunotransfer protocol, produced using a murine esophageal epithelial antigenic extract, was optimized to obtain better definition of the immunoreactive bands and better sensitivity, and three different configurations, either by the method of separation of the antigenic proteins (electrophoresis under native or denaturing conditions) or by dilution of the sera analyzed, were then validated from a diagnostic standpoint with a broad series of sera representative of rheumatological pathology.

It became apparent that, under these three conditions, the diagnostic sensitivity of the test fluctuated around 50% for a specificity in the region of 95% when only the presence or absence of immunoreactivity was taken into account.

In contrast, the antigenic protein migrating between two reference standards of molar masses 140 kD and 67 kD after separation of the antigen under native conditions, recognized much more specifically by the sera of patients suffering from RA, enabled these sera to be detected with a sensitivity of 68% for a specificity of 99%, a performance greatly superior to that of indirect immunofluorescence, which possesses a sensitivity of 43% for a specificity of 99%.

A parallel approach applied to the antigen extracted from human epidermis enabled it to be shown that the 40-kD protein, the only immunoreactive form in this tissue, made it possible to obtain diagnostic performances equivalent to those of the murine antigenic protein migrating between two reference standards of molar masses 140 kD and 67 kD.

The invention also relates to a method for purifying the autoantibodies specifically present in patients suffering from RA, characterized in that it comprises at least the following steps:

bringing a biological fluid of a patient suffering from RA into contact with at least one antigen according to the invention, and/or with human profilaggrin or filaggrin, or with the fractions thereof or the peptide fragments thereof as defined in the foregoing, under conditions that permit the formation of immunological complexes with said antibodies;

isolating said complexes from the reaction medium;

separating the autoantibodies from the immunological complexes.

The invention also relates to a method for preparing antibodies, characterized in that at least one of the antigens (proteins, protein fractions or peptide fragments) of the invention is used as an immunogen. These antibodies can correspond to antisera, to purified polyclonal antibodies, or to monoclonal antibodies produced by any hybridoma prepared according to the standard methods of cell fusion between spleen cells, activated in vitro with the antigen or originating from an animal immunized against one of the antigenic proteins of the invention, and cells of a myeloma line.

The invention also encompasses a method for preparing monoclonal or polyclonal antibodies, characterized in that human profilaggrin or filaggrin is used as an immunization antigen, and in that the antibodies that also recognize the antigen of rat esophageal epithelium are collected.

The invention also relates to a method for preparing anti-idiotype antibodies, which method is characterized in that it comprises a step during which an animal is immunized with a monoclonal or polyclonal antibody obtained according to the invention.

The invention also relates to a method for producing human monoclonal antibodies, which method is characterized in that it comprises a step during which, from lymphocytes originating from patients suffering from RA, the clones are selected which secrete antibodies which recognize at least one of the antigens (proteins, protein fractions or peptide fragments) of the invention, and/or human profilaggrin or filaggrin.

The invention also relates to a method for purifying human anti-idiotype monoclonal antibodies, which method is characterized in that it comprises a step during which, from lymphocytes originating from patients suffering from RA, the clones are selected which specifically recognize the human monoclonal antibodies obtained by the method described above, or autoantibodies specific to RA and purified by the method according to the invention.

It is self-evident that the invention also relates to all the antibodies obtained by the above methods.

Such antibodies may be used, in particular, for research purposes, to study the immunological mechanisms associated with RA, and in the development of treatments.

They may also be used to localize and characterize antigens possessing characteristics similar to those of the antigens of the invention; in particular, antigens which may be present in malpighian epithelia and in the articular tissues of mammals, including mammals of species other than man or rat.

Other features and advantages of the invention will become apparent on reading the examples which follow, and which are illustrated by the appended figures, it being understood that these examples cannot be interpreted as tending to reduce the scope of the claims.

EXAMPLE 1

CHARACTERIZATION OF THE ANTEGEN EXTRACTED FROM RAT ESOPHAGEAL EPITHELIUM

I—MATERIALS AND METHODS

A)—EXTRACTION OF EPITHELIAL PROTEINS

1) Preparation of the esophageal epithelium by chorioepithelial cleavage

The rat esophagus is composed of three main tunicae, which are, from outside to inside: a connective tissue layer (the adventitia), a muscular layer (the muscularis) and a layer composed of a chorion covered with a cornified malpighian epithelium (the mucosa).

After removal of the adventitia and the muscularis by dissection, the epithelium is separated mechanically from the chorion (chorioepithelial cleavage) after thermal shock successively at 4° C. and then at 57° C. in a liquid medium (8.5 mM $KH_2PO_2/K_2HPO_4$; 150 mM NaCl; 5 mM ethylenediaminetetraacetic acid (EDTA); 4 mM phenylmethylsulfonyl fluoride (PMSF); pH 7.4). The cleaved epithelia are stored hydrated with a minimal volume. of PBS (8.5 mM $KH_2PO_4/K_2HPO_4$; 150 mM NaCl; pH 7.4) before undergoing a histological check enabling the absence of contaminating chorion to be verified.

2) Extraction of epithelial proteins a) Buffers and extraction sequences

Since the antigen of the invention is exclusively epithelial, the extractions are carried out using the epithelium alone.

Starting with cleaved epithelia, extraction of the epithelial proteins is carried out successively by grinding in a Potter followed by agitation at 4° Celsius.

Standard protocols (W. W. Franke et al., J. Mol. Biol., 153:933–959, 1981—T. T. Sun and H. Green, J. Biol. Chem.

253(6):2053–2060, 1978) adapted to the sequential extraction of proteins from epithelial tissues, and in particular epidermis, were initially used. Extractions in a single step were then tested subsequently. Various extraction media corresponding to Tris-HCl buffers with or without the addition. of salts (KCl, NaCl), detergents (Triton, Nonidet P40 [NP40]), denaturing agents (urea, SDS) and reducing agents (betamercaptoethanol [2-ME]) were thus tested.

During the fractional extractions, the antigen was to be found exclusively in the fraction corresponding either to a Tris buffer of low ionic strength, or to a Tris-buffered saline (TBS) with the addition of EDTA and Triton. This enabled it to be confirmed that the antigen is not a cytokeratin, to show that it is extractable in the absence of urea and reducing agents and that it is water-soluble.

However, on comparing the various extraction techniques, the intensity of the immunoreactivity was seen to be greater in the presence of NP40. An extraction medium consisting of TBS+inhibitors+0.5% NP40 is hence seen to be most effective.

During the purification of the antigen, the intense absorption of NP40 at 280 nm interferes with that of the proteins, in particular in gel filtration chromatography. A TBS buffer+inhibitor without NP40 may be used for extraction of the antigen prior to purification work.

b) Optimization of the physical extraction conditions

In order to optimize the extraction procedure, certain physical parameters were explored systematically. These were temperature, time, type of grinding, type of agitation and the action of enzyme inhibitors.

Grinding:

This was performed either in an electric Potter at high speed or, more gently, in a manual Potter. The efficiency of extraction was roughly equivalent in both cases. The electric Potter is, however, preferred since it enables a larger number of esophagi to be ground.

Sonication:

Optimization of the extraction by sonications of variable duration after Potter treatment was tested. It proved to be very slight. Hence sonication is not necessary.

Agitation:

Gentle agitation and rapid agitation were compared. A rapid agitation in the presence of a detergent leading to foam formation causes excessive oxygenation of the medium, liable to degrade the antigen. In fact, the quality of the extraction was identical in both cases. A gentle agitation was, however, adopted in order to preserve the antigen as much as possible.

Temperature:

Room temperature and a temperature of 4° Celsius were compared. Better results were obtained with extractions performed at 4° Celsius.

Time:

Extractions with agitation of 15 minutes, 2 hours and 17 hours were compared. Although an increase in the extraction time slightly increases the amount of antigen extracted, a time of 15 minutes was adopted in order to minimize the risk of degradation of the antigen.

Inhibitors:

The protective effect for the antigen of the following inhibitors was tested:

Inhibitor of bacterial proliferation: sodium azide,

Inhibitor of lytic enzymes:

proteases (aprotinin, PMSF), phosphatases (NaF, PCMB (para-chloromercurybenzoic acid)), glycosidases (deoxymannojirimycin, deoxyjirimycin).

Extractions without inhibitors were carried out, in particular when the extract was intended for the biochemical characterization of the antigen by the action of different enzymes; no modification of the antigen was observed in the absence of inhibitor.

Optimized extraction protocol:

A study of the above parameters enabled the optimized extraction protocol below to be determined:

Substrate: rat esophageal epithelium obtained by chorioepithelial cleavage.

Buffer: 40 mM Tris-HCl 150 mN NaCl 10 mM EDTA pH 7.4

Inhibitors: 0.1% Sodium azide 1 mM PMSF

Aprotinin 2 $\mu$g/ml

Substrate/buffer ratio:

500 $\mu$l of buffer per esophageal epithelium

Conditions:

Grinding: electric Potter, 15 minutes

Grinding temperature: 4° Celsius

Agitation after grinding: 15 minutes at 4° Celsius

Total protein concentration of the extract:

5 to 8 mg/ml

Storage of the crude extract:

−20° or −40° Celsius

Preparation from whole esophageal mucosa:

With the object of simplifying the extraction procedure, extraction of the antigen from whole esophageal mucosa was studied. A simple dissection of the mucosa without chorioepithelial cleavage was carried out. The protein contamination of the extract thereby induced, was studied.

Parallel extractions, either from mucosae or from cleaved epithelia, were performed.

SDS-PAGE analysis of the extracted proteins shows that the presence of chorion does not lead to major protein contamination in the region of the molar mass of the antigen. After immunotransfer of the epitheliochorionic fraction extracted by grinding, the antigen is fully detectable.

c) Concentration of the crude extract

Since the antigen is poorly represented in the crude extract (less than 1% of the total proteins), a step of concentration of the extracts proves necessary, most especially when the latter are to be analyzed by miniaturized electrophoresis of the "Pharmacia® Phastsystem" system type (sample sizes of the order of one microliter).

Among the various concentration techniques tested, the one that consists in concentrating the extracts by precipitation with 10% TCA was adopted. This technique, which is easy to carry out, does not produce any degradation of the antigen, since the immunological response is fully preserved in immunotransfer.

Likewise, ethanol or ammonium sulfate precipitations as well as controlled lyophilization induce no substantial degradation of the antigen, and are hence entirely applicable.

B—ELECTROPHORESIS

Irrespective of the extraction media studied (as described above), the soluble proteins are separated by PAGE and then electrotransferred onto nitrocellulose.

1) Separation by horizontal IEF

Gel: 9×15 cm, 4% acrylamide containing ampholines forming a pH gradient from 3.5 to 9.5.

Sample applied: crude extract prepared according to the above protocol, concentrated by precipitation with 10% TCA and taken up in water.

2) One-dimensional electrophoresis

Conventional vertical electrophoresis according to the method described by Laemmli (Nature, 227: 680–685, 1970)

Gel: 10×10 cm, 7% acrylamide.

Migration buffer: 25 mM Tris, 192 mM glycine, 1% SDS, pH 8.3.

Sample applied: crude extract, lyophilized and taken up in 10 mM Tris-HCl pH 7.4, 2% SDS, 1% 2-ME, 0.1% bromophenol blue, 10% glycerol.

Miniaturized horizontal electrophoresis under denaturing conditions.

Gel: 4×4 cm, 7.5% acrylamide.

Buffer: 200 mM Tris, 200 mM tricine, 0.55% SDS, pH 8.1.

Sample applied: crude extract, concentrated by precipitation with 10% TCA and taken up in 10 mM in Tris-HCl pH 7.4, 2% SDS, 1% 2-ME, 0.1% bromophenol blue.

Miniaturized horizontal electrophoresis under native conditions.

Gel: 4×4 cm, gradient from 8 to 25% of acrylamide.

Migration buffer: 250 mM Tris, 880 mM L-alanine, pH 8.8.

Sample applied: crude extract, concentrated by precipitation with 10% TCA and taken up either in water, or in 200 mM Tris-HCl buffer at different pH values.

3) Two-dimensional IEF/SDS-PAGE electrophoresis

First dimension: horizontal IEF.

Gel: 4×4 cm, 4% acrylamide, pH gradient 3.5 to 9.5.

Sample applied:crude extract, concentrated by precipitation with ethanol (4 volumes) and taken up in water.

Second dimension: denaturing electrophoresis as described above.

Sample applied: IEF gel lane incubated in 112 mM Tris, 112 mM acetic acid, 2.5% SDS, 1% 2-ME.

C—IMMUNODETECTION

The immunodetection of the antigen is carried out using human sera originating from patients suffering from RA, in which the autoantibodies to rat esophagus stratum corneum have previously been titrated by semiquantitative IIF and assigned a titer value from 0 to 8: GIFRE (Immunofluorescence-Rat Esophagus) parameter. The threshold value, GIFRE=2, which corresponds to a diagnostic specificity for RA of greater than 99%, enables the sera of patients to be classified in two groups: GIFRE+ and GIFRE− (C. Vincent et al., Ann. Rheum. Dis. 48:712–722, 1989).

In the sera chosen, account was also taken of the following immunological parameter: the titer of class G autoantibodies to epidermal cytokeratins, determined in ELISA (GELISA) (G.Serre et al., J. Invest. Dermatol. 88:21–27, 1987). These autoantibodies react in immuno-transfer with the contaminating human cytokeratins which may be present in the extract and due to the natural desquamation of the technicians. The sera used were chosen to constitute two groups also, GELISA+ and GELISA−, in accordance with the high titer (absorbance>0.6) or low titer (absorbance<0.2) of these natural autoantibodies. In total, the following four subgroups of RA sera were used:

GIFRE+/GELISA+
GIFRE+/GELISA−
GIFRE−/GELISA+
GIFRE−/GELISA−

Lastly, control sera originating from normal individuals or from patients suffering from non-rheumatoid rheumatological disorders, as well as murine monoclonal antibodies specific for human cytokeratins, were included in the tests. (G. Serre et al., INSERM Colloquium, John Libbey Eurotext, Vol. 171:524, 1988).

After PAGE of the proteins, immunotransfer onto nitrocellulose membranes and incubation with the human sera or the monoclonal antibodies, a second, peroxidase-labeled antibody, corresponding to a F(ab')$_2$ fragment of goat anti-human IgG (gamma) or Fab fragment of sheep anti-mouse IgG (H+L), is incubated with the membrane, and formation of the antigen-antibody complex is visualized by demonstrating the peroxidase activity with $H_2O_2$ and 4-chloro-1-naphthol.

Under these experimental conditions, the antigen is identifiable in immunotransfer by a specific immuno-reactivity of the GIFRE+ RA sera. The natural anticytokeratin autoantibodies manifest themselves, only when the antigen has previously been separated in SDS-PAGE, by the presence of immunoreactive bands located around 65–67 kD, present in only the GELISA+ sera, more or less intense in accordance with their titer and completely independent of the GIFRE value.

D—CHROMATOGRAPHY

The antigenic molecules were separated into different fractions after sequential gel filtration/hydrophobic interaction chromatography. These fractions were analyzed by SDS-PAGE and PAGE under native conditions.

E—ENZYMATIC DIGESTION

1) Proteinase K

Two extracts of rat esophageal epithelium in TBS/NP40 buffer are precipitated with 10% TCA, and the proteins are taken up in 50 mM Tris-HCl buffer pH 7.5, 10 mM $CaCl_2$. One of the extracts is treated with proteinase K (preincubated for 1 hour at 37° C. in order to remove other hydrolases which may be present in the commercial preparation) at a final concentration of 50 $\mu$g/ml. Both samples are then incubated for 1 hour at 37° C. and thereafter analyzed comparatively in immunotransfer after migration in PAGE under native conditions or in SDS-PAGE.

2) Nuclease

Two extracts of rat esophageal epithelium in TBS/NP40 buffer are precipitated with 10% TCA. One of them is hydrolyzed with 2 U/$\mu$l micrococcal nuclease (hydrolysis of DNA and RNA) in 50 ml Tris-HCl pH 7.5, 5 mM $CaCl_2$. The second, untreated sample serves as a control. Both preparations are incubated for 1 hour at 37° C. and then analyzed comparatively in immunotransfer after migration in PAGE under native conditions or in SDS-PAGE.

F—DEGLYCOSYLATION

1) Oxidation with periodic acid

The protocol of WOODWARD et al. (J. IMM. METH. 78:143–153, 1985) was used; this protocol permits the periodic oxidation of a sample previously transferred onto a nitrocellulose membrane, it being possible for the periodic oxidation to be followed by an immunodetection.

An extract of rat esophageal epithelium is transferred after migration in SDS-PAGE. The nitro-cellulose membrane is cut up into several lanes, which are subjected to periodic oxidation (incubation in 50 mM sodium acetate buffer pH 4.4, 20 mM sodium periodate, for 1 hour in the dark and at room temperature) followed by reduction with 50 mM sodium borohydride ($NaBH_4$) in PBS pH 7.4 for 30 minutes at room temperature. Control samples which do not undergo any chemical treatment or which undergo only the reduction are included. Immuno-detection is then carried out on all the samples.

2) Treatment with trifluoromethanesulfonic acid TFMS)

The use of TFMS according to the method of EDGE et al. (ANAL. BIOCHEM. 118:131–137, 1981) permits a virtually total deglycosylation of glycoproteins while preserving their peptide backbone. This method was applied to a control glycoprotein, bovine fetuin, and to extracts of rat esophageal epithelium containing the antigen. The extracts are dialyzed against water and then lyophilized. Their treatment is carried out by adding a mixture (66:33 V/V) of TFMS and anisole (agent protecting the peptide backbone), and incubating with agitation after saturating the atmosphere of the tubes with nitrogen. The reference protocol was optimized by varying different parameters:

proportion of TFMS/anisole mixture relative to the mass of proteins treated: 33 to 266 µl of mixture per mg of total protein in the esophageal extract.

temperature: 0° C., 4° C. or room temperature.

incubation time: 1, 3 or 24 hours.

In all cases, after incubation, the reaction is stopped by adding 2 volumes of absolute ether and 3 volumes of a pyridine/water (50:50 V/V) mixture. The precipitate of pyridinium trifluoromethanesulfonate, which is soluble in the ether phase, is removed therewith. After a further extraction with absolute ether, the aqueous phase is dialyzed with water. The samples are then lyophilized, separated by PAGE, transferred and thereafter immunodetected.

3) Treatment with peptide N-glycosidase F (PNGase F)

PNGase F, also marketed under the name Glycopeptidase F or N-Glycanase, hydrolyzes the amide bond situated between the asparaginyl residue of a glycoprotein and the N,N'-diacetylchitobiose of the structure common to all N-linked oligosaccharides.

Fetuin contains three N-linked oligosaccharide chains, the removal of which with PNGase F leads to a decrease in molar mass which can be readily visualized in SDS-PAGE (S. HIRANI et al., ANAL. BIOCHEM. 162:485–492, 1987).

Bovine fetuin (2 mg/ml) and a lyophilized extract of rat esophageal epithelium (8 mg/ml of protein) are denatured for 5 min at 90° C. with 2% SDS and 0.05M 2-ME. The proteins are then placed in a reaction medium of the following composition:

1.25% NP40 (protection of the enzyme against the denaturing action of SDS), 166 mM potassium phosphate pH 8 (preservation of the optimal pH of the enzyme), 10 mM 1,10-ortho-phenanthroline (protease inhibitor) solubilized in methanol at a final concentration of 10%, PNGase F 0.3 U/µl.

In this reaction medium, the respective final concentrations of SDS and of 2-ME are 0.166% and 16 mM. Incubation is for 24 hours at 37° C.

"Fetuin" and "antigenic extract" controls incubated without enzyme are included in the protocol. After hydrolysis and concentration by precipitation with TCA, the samples are separated by PAGE, transferred and immunodetected.

G—REACTIVITY WITH DIFFERENT LECTINS

The Inventors sought to confirm the glycoprotein nature of the antigen by detecting certain sugars specifically with lectins coupled to peroxidase. Two plant lectins, namely wheatgerm lectin (WGA) and concanavalin A (ConA) were chosen for their differing specificities (I. J. GOLSTEIN and R. D. PORETZ, The Lectins: properties, functions and applications in biology and medicine):

WGA recognizes N-acetyl-β-D-glucosamine residues with the following increasing affinities :

(1) GlcNAc<<GlcNAcβ1-4GlcNAc<GlcNAcβ1-4GlcNAcβ1-4GlcNAc and also binds with lower affinity to sialic acid residues.

ConA combines with the following sugars, classified by increasing affinity:

(2). αGlcNAc<αGLc<αMan<Manα1-2Man<Manα1-2Manα1-2Man.

The proteins of two antigenic extracts, crude or purified, are transferred onto nitrocellulose after migration in one-dimensional PAGE or IEF/SDS-PAGE. The nitrocellulose bands are incubated with ConA and WGA coupled to peroxidase at the respective minimal concentrations of 20 and 15 g/ml (J. C. S. CLEGG, ANAL. BIOCHEM. 127:389–394, 1982 and W. F. GLASS et al., ANAL. BIOCHEM. 115:219–224, 1981.) Incubation is carried out in a 50 mM Tris-HCl buffer pH 7.4, 200 mM NaCl, 1 mM $CaCl_2$, 1 mM $MnCl_2$ and 0.1% Tween for 1 hour at 37° C. and overnight at 4° C. The incubation is preceded and followed by steps of washing in the same buffer. Various additional saturating agents, such as gelatin or bovine serum albumin oxidized by periodic acid treatment, do not enable the response obtained when using Tween alone to be amplified. After the final wash, the lectin-antigen combination is visualized by demonstrating the peroxidase activity with $H_2O_2$ and 4-chloro-1-naphthol as in the immunodetections.

II—PHYSICOCHEMICAL CHARACTERIZATION OF THE ANTIGEN

The physicochemical characterization of the antigen was performed using crude extracts of rat esophageal epithelium, and then using purified antigen fractions. In both cases, after electrophoretic separation, the proteins were transferred and then immunodetected with sera of patients suffering from RA.

A—MOLAR MASS

FIG. 1 shows the immunotransfer analysis of an extract of rat esophageal epithelium separated by SDS-PAGE. The crude extract is concentrated tenfold by precipitation with 10% TCA, taken up in Laemmli buffer, separated by SDS-PAGE (7.5%), transferred onto nitro-cellulose and immunodetected with GIFRE+ (lanes 1–12) and GIFRE– (lanes 13,14) RA sera diluted to 1/100; "$C_0$" denotes a negative control incubated with the secondary antibody alone, and "MW" denotes molecular weight markers. The antigen takes the form of a narrow immuno-reactive band corresponding to a protein of average molar mass approximately 210 kD and a broad and spread immuno-reactive region corresponding to a protein of average molar mass between 90 and 130 kD.

B—ISOELECTRIC POINTS

The crude extract is concentrated fivefold by precipitation with 10% TCA, taken up in water, separated by IEF (pHi 3.5 to 9.5), transferred and then immunodetected with GIFRE+ and GIFRE– sera of patients suffering from RA. The antigenic molecules exhibit a very heterogenous distribution; the proteins of the crude extract which are recognized specifically by most of the GIFRE+ sera distribute in a cluster of fine bands whose isoelectric points vary from 5.2 to 7.5.

C—MIGRATION CHARACTERISTIC UNDER NATIVE CONDITIONS

Figure 2:
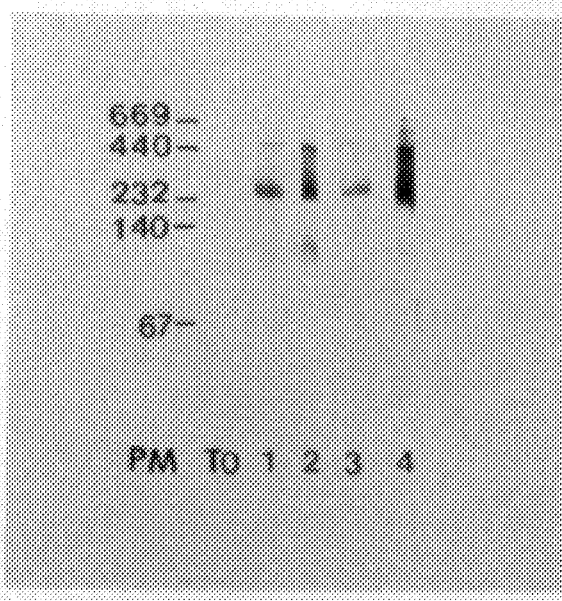
FIG. 2 shows the immunotransfer of an extract of rat esophageal epithelium taken up in an acid medium and separated by PAGE under native conditions.

FIG. 2 shows the immunotransfer of an extract of rat esophageal epithelium taken up in an acid medium and separated by PAGE under native conditions. The crude extract, concentrated tenfold by precipitation with 10% TCA, is taken up in water (pH below 4), separated by PAGE under native conditions (8–25%), transferred and then immunodetected with GIFRE+ RA sera (lanes 1–4) diluted to 1/100; "$C_0$" denotes a negative control incubated with the secondary antibody alone. Under these conditions of taking up the sample at acid pH, immunotransfer performed with four sera of patients suffering from RA brings out three immunoreactive regions corresponding, respectively, to:
- a first protein which migrates like horse spleen ferritin (molecular weight: 440 kD),
- a second protein which migrates like ox liver catalase (molecular weight: 232 kD),
- a third protein which migrates between ox heart lactic dehydrogenase and bovine serum albumin (respective molecular weights: 140 kD and 67 kD),
- which regions are recognized with variable affinity according to the serum.

D—TWO-DIMENSIONAL IEF/SDS-PAGE ELECTROPHORESIS

This technique, which combines IEF in the first dimension and SDS-PAGE in the second, enables the isoelectric points and the molar masses of the various antigenic molecules to be determined simultaneously, their great charge heterogeneity to be confirmed and their great mass heterogeneity to be demonstrated.

Figure 3:
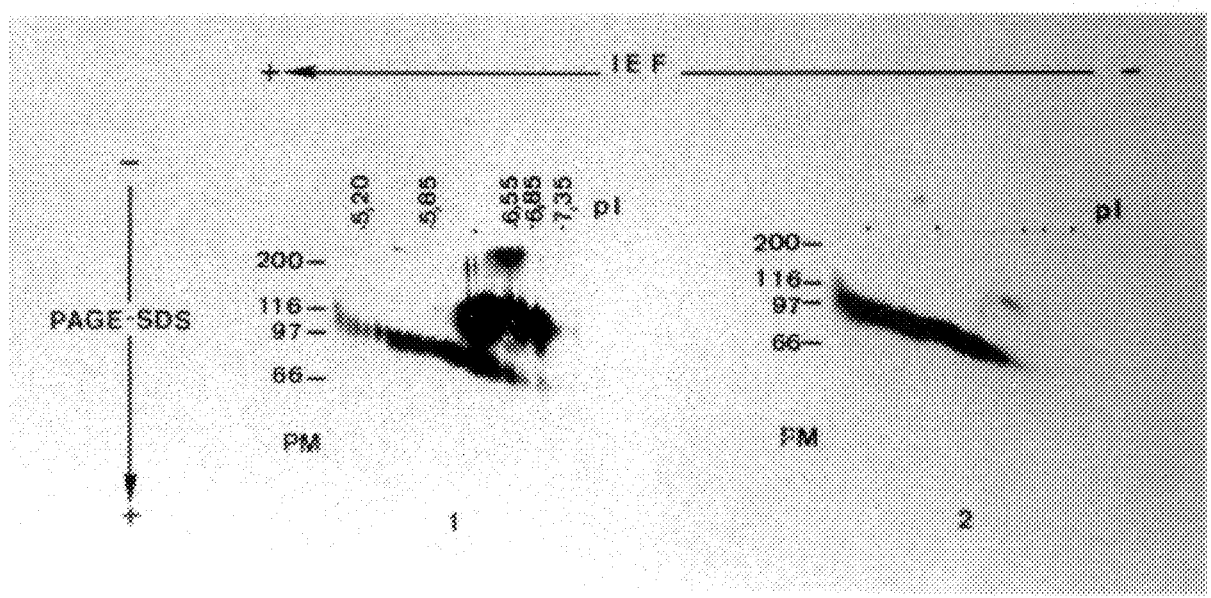
FIG. 3 shows the immunotransfer of an extract of rat esophageal epithelium separated by two-dimensional (IEF/SDS-PAGE) electrophoresis.

FIG. 3 shows the immunotransfer of an extract of rat esophageal epithelium separated by two-dimensional (IEF/SDS-PAGE) electrophoresis. The crude extract, concentrated twentyfold by precipitation with ethanol and then taken up in water, is separated by IEF (pHi 5 to 8) and then by SDS-PAGE (7.5%), transferred and then immunodetected with two GIFRE+ (1,2) sera of patients suffering from RA, diluted to $\frac{1}{100}$. The immunoreactive region from 90 to 130 kD possesses pHi values varying from 5.85 to 7.35; those of the 210 kD band vary from 5.85 to 6.85. A third immunoreactive population, in the shape of a "comma", migrates from 120 to 67 kD while these pHi values distribute in continuous fashion between 5 and 7.5. The antigenic molecules of molar mass less than 90 kD, clearly detected after two-dimensional electrophoresis, are seen in one-dimensional electrophoresis only with sera of high titer, in the form of an extension of the immunoreactivity towards the regions of low molecular weight. The larger amount of antigen applied in IEF/SDS-PAGE, permitting greater sensitivity of immunodetection, explains this apparent disparity.

E—CHROMATOGRAPHIC SEPARATION CHARACTERISTICS

Figure 4:
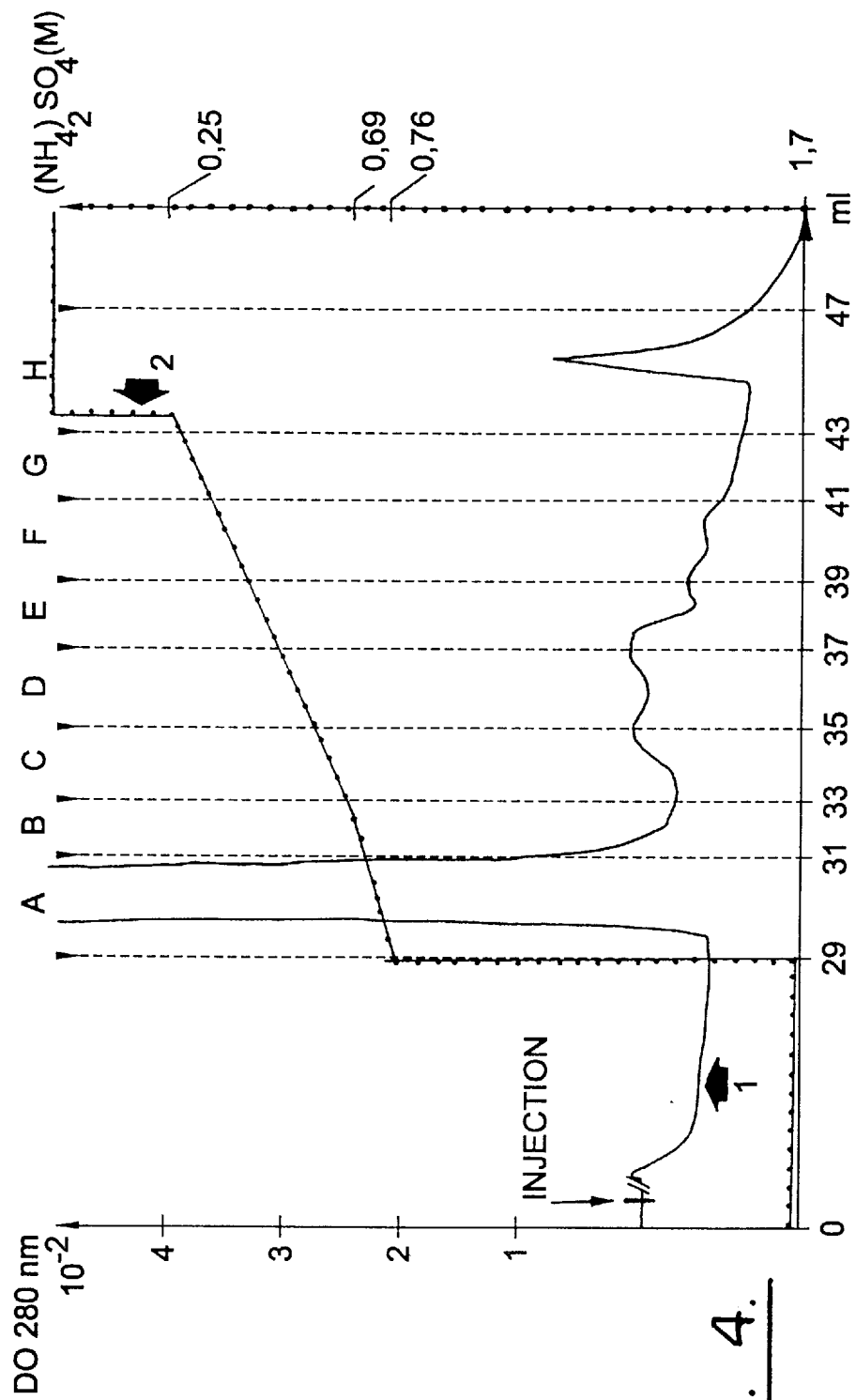
FIG. 4 shows the separation in hydrophobic interaction chromatography of an antigen solution repurified from a crude extract by gel filtration chromatography.

FIG. 4 shows the separation in hydrophobic interaction chromatography of an antigen solution repurified from a crude extract by gel filtration chromatography- on Superose 12 (elution profile followed by measurement of absorbance at 280 nm). Immunoreactive fractions thus prepurified are separated on Phenyl-Superose (Line 2=Equilibration buffer: 50 mM phosphate, 1.7M $(NH_4)_2SO_4$, pH 7; Elution buffer: 50 mM phosphate pH 7; injected volume: 3.6 ml; flowrate: 0.5 ml/min; OD 280 nm full scale (Line 1): 0.05).

The elution profiles and the immunotransfer study of the different antigenic fractions proved very reproducible during a large number of purifications. The distribution of the antigenic molecules in the different fractions could hence be modelled.

FIG. 5 shows the modelling, obtained after SDS-PAGE (FIG. 5A) or PAGE under native conditions (FIG. 5B), of the immunoreactivity profiles of the antigenic fractions purified by sequential gel filtration/hydrophobic interaction chromatography. The differences in intensity of the immunoreactive bands or regions reflect the relative abundance of antigenic proteins in each fraction (A–H).

In denaturing electrophoresis, the band at 210 kD (fractions F, G and H), the broad, poorly demarcated band from 90 to 130 kD (fractions D, E, F, G and H) and a band from 67 to 90 kD (fractions C, D and E) were visualized.

In electrophoresis under native conditions, the fine band at 440 kD (fractions F, G and H), the band at 232 kD (fractions C, D, E, F, G and H) and the broad band between 140-kD and 67-kD reference standards (fractions B, C, D and E) were to be found.

Comparison of the antigenic molecules analyzed in SDS-PAGE in the different purified fractions (FIG. 5) and the molecules identified after two-dimensional (IEF/SDS-PAGE) electrophoresis in a crude extract, as shown in FIG. 3, provides information about their respective hydrophobicity:
- The band at 210 kD whose pHi values vary from 5.85 to 6.85 is to be found in the fractions obtained at the end of elution (fractions F, G and H); it is hence very hydrophobic.
- The diffuse region from 90 to 130 kD whose pHi values are located from 5.85 to 7.35 possesses the same elution profile as the band at 210 kD (fractions E, F, G and H), and hence the same hydrophobicity.
- In contrast, the population in the shape of a "comma" which possesses a wider spread of pHi values from 5 to 7.5 is to be found predominantly at the beginning of elution (fractions B, C, D and E) and hence possesses a less hydrophobic character than the above two molecules.

III—BIOCHEMICAL CHARACTERIZATION OF THE ANTIGEN

A—THE ANTIGENIC MOLECULES ARE PROTEIN IN NATURE

FIG. 6 shows the immunotransfer analysis of the proteins in an antigenic extract digested (b) or not digested (a) with proteinase K, separated by PAGE under native conditions (8–25%), transferred and then immunodetected with three GIFRE+ sera of patients suffering from RA (lanes 1–3) and one GIFRE– serum of a patient suffering from RA (lane 4); $C_0$ denotes a negative control incubated with the secondary antibody alone.

Ponceau red staining of the nitrocellulose bands corresponding to the treated samples shows the total digestion of the proteins in the extract. Immunodetection after PAGE under native conditions shows that the specific immunoreactivity of the GIFRE+ sera disappears when the sample is previously digested with proteinase K. Immunodetection after transfer of the samples separated in SDS-PAGE confirmed this result.

Having affirmed the protein nature of the molecules bearing the antigenicity, the Inventors undertook a determination of whether the proteins were homo- or heteroproteins, of the combinations and/or substitutions of the antigen which were capable of accounting for the diversity of isoelectric point and of apparent molar mass, and of the biochemical nature of the epitope or epitopes recognized.

B—THE ANTIGENIC PROTEINS ARE NOT COMBINED WITH NUCLEIC ACIDS

The possible combination of the antigen with nucleic acids was studied. FIG. 7A the analysis of an extract of rat esophageal epithelium treated (b) or not treated (a) with micrococcal nuclease, and then analyzed by electrophoresis in 1% agarose gel followed by staining with ethidium bromide; "M" denotes a size marker in kilobase pairs.

After separation of the samples by electrophoresis in 1% agarose gel, the absence of nucleic acids in the treated sample demonstrates the efficacy of the enzymatic digestion.

FIG. 7B the immunotransfer analysis after PAGE under native conditions (8–25%), carried out with three GIFRE+ sera of patients suffering from RA (lanes 1–3) and one GIFRE– RA serum (lane 4); $C_0$ denotes a negative control incubated with the secondary antibody alone.

Immunodetection after PAGE under native conditions shows the insensitivity of the antigenic proteins to treatment with the nuclease, both from the standpoint of their immunoreactivity with the sera of RA patients and from that of their apparent molar mass, demonstrating that they are not combined with nucleic acids.

C—ARE THE ANTIGENIC PROTEINS GLYCOPROTEINS?

Glycoproteins often exhibit a great heterogeneity of isoelectric points, and an inconsistent level of binding of SDS which makes their resolution in SDS-PAGE mediocre. Since the antigenic proteins also possess these characteristics, the Inventors investigated their possible substitution with carbohydrate residues. For this purpose, techniques aimed either at degrading the sugar molecules possibly borne by the peptide backbone, or at relieving the protein portion of its glycan residues, were studied.

1) Destruction of possible carbohydrate epitopes with periodic acid

FIG. 8 shows the immunodetection of an extract of rat esophageal epithelium which, after separation by SDS-PAGE (7.5%) and transfer, was:

incubated for 1 h 30 min in PBS buffer ("incubation" control: lane a), incubated for 1 h in sodium acetate buffer and then reduced for 30 minutes with sodium borohydride ("reduction" control: lane b), oxidized with periodic acid in sodium acetate buffer for 1 h and then reduced for 30 minutes with sodium borohydride ("test": lane c); three GIFRE+ RA sera (lanes 1–3), two GIFRE– RA sera (lanes 4,5) and two control sera (lanes 6,7) were used; "C$_0$" denotes a negative control incubated with the secondary antibody alone.

Treatment with periodic acid in no way modified the proteins specifically recognized by the sera of patients suffering from RA. Three interpretations of this result are possible:

the antigenic proteins are glycoproteins, but the sugars sensitive to periodic oxidation which they bear are not involved in the epitope or epitopes predominantly recognized by the autoantibodies specific to RA.

the antigenic proteins are glycoproteins, but the sugars which they bear, by virtue of their nature and/or their type of linkage, are insensitive to periodic oxidation (periodic acid cleaves the bond between two vicinal carbons either each initially bearing an alcohol function, or one initially bearing an alcohol function and the other an acid or ketone or primary or secondary amine function).

the antigenic proteins are not glycoproteins.

In order to distinguish between these three possibilities, the Inventors used a method of total deglycosilation and then investigated modifications of the mass or immunoreactivity of the antigenic properties.

2) Dealycosilation

Two main types of link permit the combination of an oligosaccharide with a peptide backbone: the O-glycoside bond which permits the combination of an oligosaccharide with a serine or threonine (and, rarely, hydroxylysine) residue via an N-acetylated galactosamine, and the N-glycoside bond which attaches an oligosaccharide to an asparagine residue via an N-acetylated glucosamine.

In order to deglycosylate glycoproteins, two types of treatment may be applied:

non-specific treatments enabling all types of carbohydrate radicals to be removed, irrespective of whether they are linked to the protein via an N-glycoside bond or an O-glycoside bond. This is the case, for example, with chemical treatment with trifluoromethanesulfonic acid (TFMS);

treatments specific for one or other of these types of bond. This is the case with β-elimination with sodium hydroxide for O-glycoside bonds, and with a number of enzymatic hydrolyses, more or less specific for the chemical nature of the N-linked sugar, for N-glycoside bonds.

a) Non-specific treatment with TFMS

Immunotransfer analysis after SDS-PAGE (7.5%) of an antigenic extract treated with TFMS and an extract incubated in water shows that the antigenic proteins exhibit a slight decrease in apparent molar mass relative to the control sample. Although small, this difference of approximately 10 to 20 kD is observed for all the conditions of treatment and is to be found in two different experiments. Immunotransfer analysis after IEF of the proteins in an extract of rat esophageal epithelium treated with TFMS shows that the specific immuno-reactivity of the sera of patients suffering from RA with the control samples spreads over a pHi region from approximately 5.2 to 7.5. After treatment with TFMS, the proteins immunodetected with sera of patients suffering from RA possessed more basic pHi values of between 6 and 8.

This change in pHi and in apparent molar mass of the antigenic proteins favors the possibility of a glycan substitution of the molecules. However, the persistence of a poor definition in SDS-PAGE and of a broad pHi range in IEF suggests that the antigenic proteins might also be substituted with other, non-carbohydrate radicals, and/or that the observed effects might be due to the cleavage of an especially labile peptide bond.

However, the preservation of the immunoreactivity after treatment with TFMS is a strong argument in favor of the non-carbohydrate nature of the epitope or epitopes recognized by the autoantibodies specific to RA.

b) Specific treatment with PNGase F

In order to confirm the results obtained with TFMS, the Inventors undertook deglycosylation experiments with the enzyme PNGase F, which specifically removes N-linked sugars.

Deglycosylation with PGNase F was performed on a crude antigenic extract after dialysis against water and lyophilization. Analysis of this extract by immunodetection in SDS-PAGE and transfer does not bring out any difference between the control antigen and the antigen treated with PNGase F. Two interpretations of this result are possible:

the antigen is not substituted with N-oligosaccharides, the oligosaccharides joined to asparagine residues of the protein have a novel chemical structure which prevents them from being cleaved by PNGase F.

However, a one-dimensional analysis alone does not permit a clear assertion of the insensitivity of the antigenic proteins to PNGase F, since these proteins partially superpose, as shown by two-dimensional electrophoretic analysis.

3) Detection of sugars with lectins

The possible reactivity of the antigen with wheatgerm lectin (WGA) or concanavalin A (ConA) was tested by "affinity detection" on nitrocellulose and compared with the specific immunodetection profiles of RA sera.

The proteins in the crude antigenic extract of rat esophagus, recognized after SDS-PAGE or PAGE under native conditions by a serum of a patient suffering from RA, were different from the proteins recognized by the lectins. However, common regions of reactivity, especially in respect of the 210-kD protein in SDS-PAGE, suggest that WGA and ConA recognize a portion of the antigen. Antigenic fractions purified by gel filtration chromatography were analyzed under the same conditions. This experiment confirmed that glycoproteins of the same molecular weight as some antigenic proteins were recognized by ConA, and that the reactivity profile of WGA appeared to resemble that of a serum of a patient suffering from RA.

The affinity of the lectins with respect to the antigenic proteins of rat esophagus was confirmed by analysis after IEF/SDS-PAGE of the crude antigenic extract.

Figure 9:
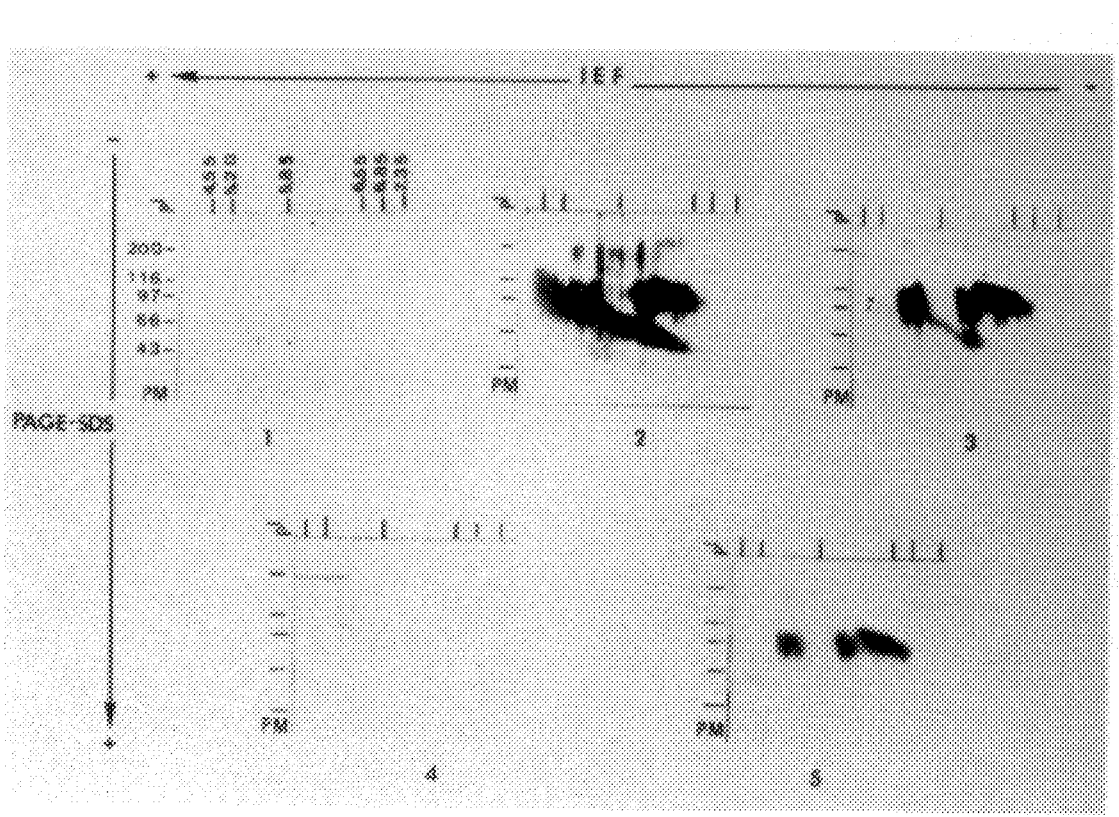
FIG. 9 shows the detection of the proteins in a crude antigenic extract, after two-dimensional electrophoresis, where panel 1 contained GIFRE− serum from a patient with rheumatoid arthritis; panels 2–3 contained GIFRE+ sera of a patient with rheumatoid arthritis; panel 4 contains ConA, and panel 5 contains WGA.

FIG. 9 shows the detection of the proteins in a crude antigenic extract, after two-dimensional electrophoresis (IEF, isoelectric point 5 to 8/SDS-PAGE, 7.5%) and transfer onto nitrocellulose, with:

in (1): a GIFRE− serum of a patient suffering from RA, in (2,3): GIFRE+ sera of a patient suffering from RA, in (4): ConA, in (5): WGA;

in order to amplify the reactivity, three applications of antigenic extract were made on the IEF gel. One fraction of the antigen (band at 210 kD and immunoreactive region between 90 and 130 kD) applied on the anode side precipitated there, producing a reactivity artifact in the acid pHi region.

This study enabled it to be shown that the molecules recognized by ConA were different from the antigen, but that WGA combined specifically with the 90–130-kD and 210-kD antigenic proteins. The immunoreactive proteins in the shape of a "comma" which spread from 120 kD to 67 kD with pHi values from 5 to 7.5 do not, in contrast, exhibit any reactivity with respect to WGA.

EXAMPLE 2

CHARACTERIZATION OF THE ANTIGENIC EXTRACTED FROM HUMAN EPIDERMIS

I—MATERIALS AND METHODS

A—PATIENTS AND SERA

The present study was carried out using 64 sera of patients suffering from various rheumatological diseases fully characterized from the clinical and biological standpoints. Of these 64 sera, 45 originate from patients suffering from RA defined according to the criteria of the American Rheumatism Association. 32 sera originating from healthy subjects, men and women, were used as a control.

Two monoclonal antibodies (MAb), one specific for human cytokeratins, designated F 12–19 (Anticytokeratin Ref. 220-81, Dept. Biosoft CLONATEC), the other specific for human filaggrin, designated AKH-1 (Catalogue Ref. BT-576, Biomedical Technologies Inc.), were used.

B—EXTRACTION OF EPIDERMAL PROTEINS

Skin fragments collected after mammary and abdominal plastic surgery or after circumcision were stored at −80° C. The epidermis was separated mechanically from the dermis according to the method described by Kassis and Sondergaard (ARCH. DERMATOL. RES. 273: 301–306, 1982), by a thermal treatment at 4° C. and then at 57° C. in PBs buffer (8.5 mM $KH_2PO_4$/$K_2HPO_4$; 150 mM NaCl) containing 5 mM EDTA and 0.5 mM PMSF, and then ground mechanically in 40 mM Tris-HCl buffer pH 7.4, 150 mM NaCl, 10 mM EDTA, 0.5% NP40, hereinafter designated buffer A.

After centrifugation at 12,000 g for 15 minutes, the supernatant was separated from the pellet containing the epidermal cytokeratins.

In addition, other extractions were carried out according to the same protocol but in a 20 mM Tris-HCl buffer pH 7.4, 0.5 mM PMSF, hereinafter designated buffer B.

The various fractions were stored at −20° C.

C—ELECTROPHORESIS

The proteins in the various fractions were analyzed by IEF at equilibrium or before equilibrium (NEpHGE), or by SDS-PAGE or PAGE under native conditions. Two-dimensional electrophoresis was also carried out.

The proteins were sometimes precipitated with four volumes of ethanol or with TCA at 15% final concentration, in order to increase their concentration.

D—IMMUNODETECTION

The proteins were transferred onto nitrocellulose membranes according to the technique described by TOWBIN et al. (PNAS 76: 4350–4354, 1979). The sera were used diluted from $1/10$ to $1/100$ after incubation of the nitrocellulose strips in PBS, 0.05% Tween 20. Incubation in the presence of the sera was continued for one hour at 37° C. and then 12 hours at 4° C.

The monoclonal antibodies AKH-1 (diluted to $1/100$) or P12-19 (diluted to $1/500$) were incubated for two hours at 37° C. After washes, the nitrocellulose strips were visualized with peroxidase-labeled anti-human or -murine IgG secondary antibodies.

E—ENZYMATIC TREATMENTS

The concentrated epidermal extract (80 $\mu g/\mu l$) was treated with proteinase K (1 mg/ml, 30 minutes, 37° C. in the presence of 1% SDS) or with micrococcal nuclease (100 U/ml, 30 minutes, 37° C. in a 30 mM Tris-HCl buffer, 5 mN $CaCl_2$, pH 8).

F—IMMUNOPRECIPITATION

The epidermal extract, preadsorbed on Protein A-Sepharose, was incubated at 37° C. for 2 h in the presence of the antibody AKH-1 or F12-19 and NaCl, 1M final concentration.

The antigen-antibody complexes formed were then collected with Protein A-Sepharose and thereafter analyzed by immunotransfer after SDS-PAGE.

G—PURIFICATION OF CYTOKERATINS

The urea-soluble cytokeratins were purified from mammary epidermis according to the method described by T. T. SUN and H. GREEN (J. Biol. Chem. 252: 2053–2060, 1978).

H—PURIFICATION OF HUMAN FILAGGRIN

Filaggrin was extracted from mammary skin according to the technique described by LYNLEY and DALE (B.B.A. 774: 28–35, 1983) with the following modifications: the epidermal extract in 6M urea, prepared in the absence of a reducing agent, was purified using FPLC chromatography with an anion exchange resin. The cationic proteins not retained were precipitated with 4 volumes of acetone, redissolved in a small volume of buffer containing 1.5% of SDS and 2.5% of 2-ME and applied to the top of an SDS-PAGE preparative gel 10 cm in height. This gel was then transferred onto a membrane of the Immobilon®-PVDF type marketed by the company MILLIPORE. The region corresponding to filaggrin was identified by immunodetection with the antibody AKH-1 and cut out; the filaggrin was then eluted with 0.3 ml/cm² of elution buffer (50 mM Tris-HCl pH 8.8, 2% SDS, 1% Triton X-100) and concentrated by precipitation.

I—PURIFICATION OF THE ANTIGEN 20 cm² of mammary epidermis were ground in an electric Potter in buffer A. The homogenate was centrifuged for 15 minutes at 10,000 g and the supernatant precipitated with TCA (15% final concentration). The precipitate was resolubilized in a small volume of 30 mM Tris-HCl pH 8, 5 mM $CaCl_2$; the soluble fraction was clarified by centrifugation, treated with 1.5% SDS and 2.5% 2-ME and applied to the top of the preparative SDS gel 10 cm in height. The antigen was then purified by elution as described above for filaggrin, the region corresponding to the antigen being identified by immunodetection with a RA serum.

II—RESULTS

A—PHYSICOCHEMICAL AND BIOCHEMICAL CHARACTERIZATION OF THE ANTIGEN

In order to characterize the antigen recognized by the RA sera, a mammary epidermal extract was prepared by homogenization of mammary epidermis in buffer A in the presence of a nonionic detergent (NP40). This soluble extract was analyzed by immunodetection after PAGE and transfer of the proteins onto nitrocellulose.

Figure 10:
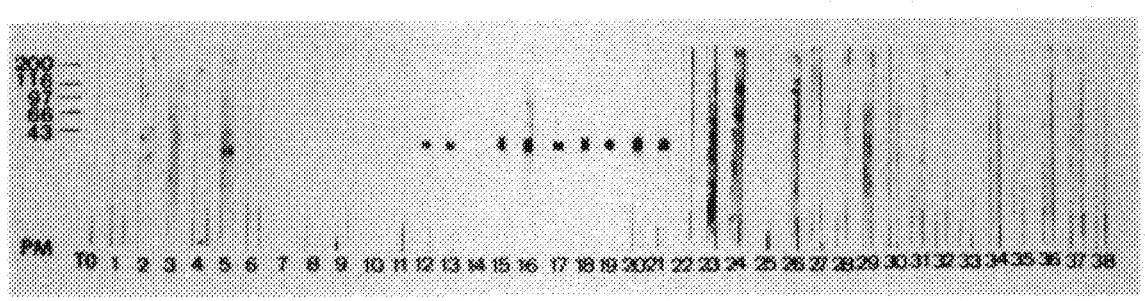
FIG. 10 shows the immunotransfer analysis of the NP40 extract with rheumatoid arthritis sera and control sera, where lanes 1 and 3 contain sera from a patient with malignant myeloma, lane 2 contains serum from a patient with Sharp's disease, lane 4 contains serum from a patient with osteoarthritis, lane 5 contains serum from a patient with polymyositis, lane 6 contains serum from a patient with Paget's disease, lanes 7–21 contain sera from patients with rheumatoid arthritis, and lanes 22–38 contain sera from healthy subjects; $C_o$ is a negative control.

FIG. 10 shows the immunotransfer analysis of the above NP40 extract with RA sera and control sera. The NP40 extract (8 mg/ml) was precipitated with TCA, taken up in Tris-CaCl$_2$ buffer, concentrating it 7-fold, and then analyzed by immunotransfer after SDS-PAGE (gradient 8–25%). The sera were diluted to ⅒ in PBS/0.05% Tween 20. Sera 1 and 3 originate from patients suffering from malignant myeloma, serum 2 originates from a patient suffering from Sharp's disease, serum 4 originates from a patient suffering from osteoarthritis, serum 5 originates from a patient suffering from polymyositis, serum 6 originates from a patient suffering from Paget's disease, sera 7 to 21 originate from patients suffering from RA and sera 22 to 38 originate from healthy subjects; "$C_0$" is a negative control incubated only with the labeled antihuman Ig antibody.

Most of the sera of patients suffering from RA (80%) recognized a protein possessing in SDS-PAGE a molecular weight of approximately 40 kD. Its migration was not modified by omission of the reducing agent (2-ME) in the sample buffer, indicating that this molecule probably does not contain a disulfide bridge. In contrast, 89% of the sera of patients suffering from a non-rheumatoid rheumatological disease and none of the control sera recognized this antigen. A 68-kD protein was detected non-specifically by a large proportion of sera belonging to all the groups tested, and therefore probably by natural autoantibodies.

Figures 11A, 11B, 12, 13:
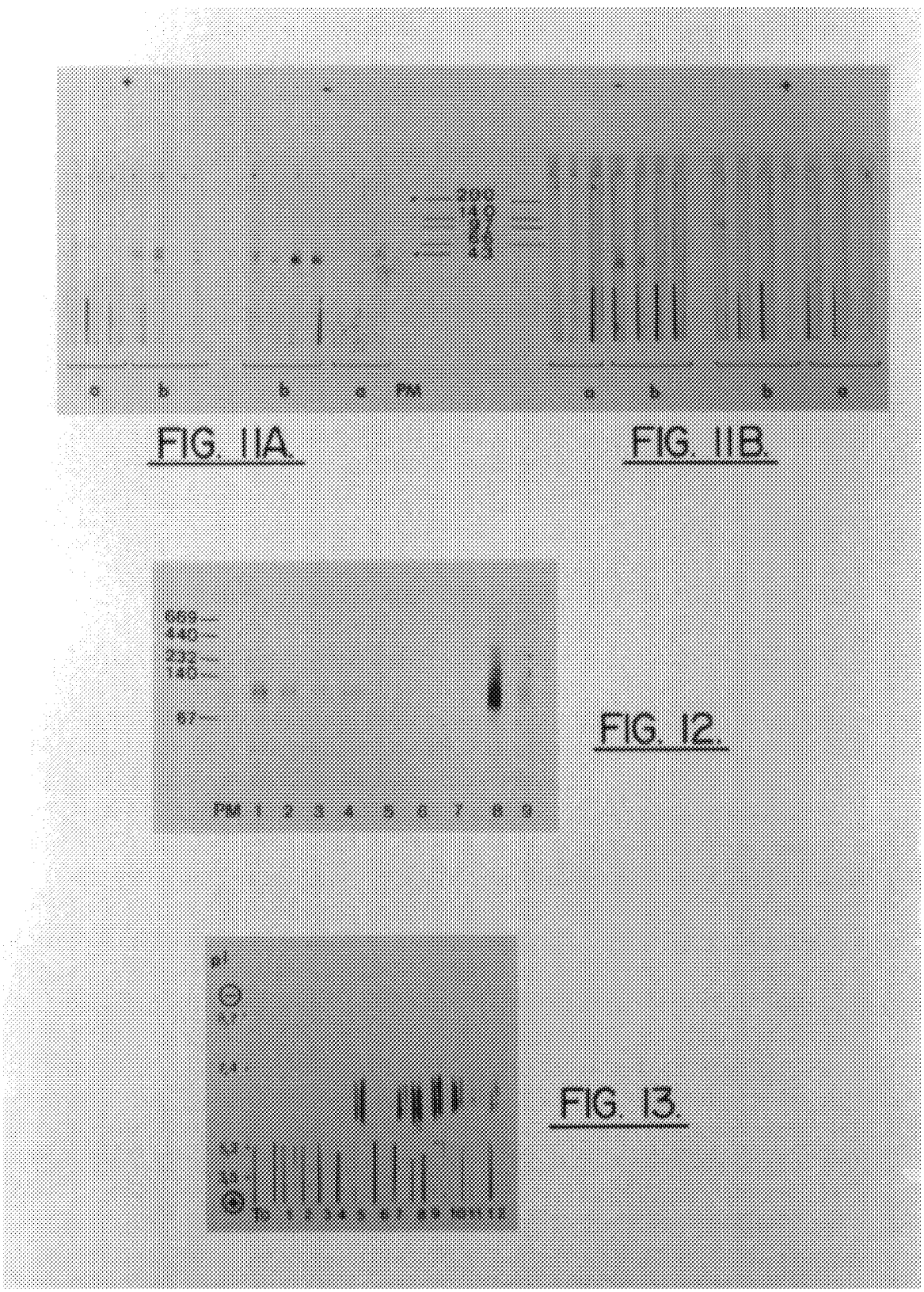
FIG. 11A shows the immunotransfer analysis of the above NP40 antigenic extract treated (+ lanes) or not treated (− lanes) with a nuclease.
FIG. 11B shows the immunotransfer analysis of the above NP40 antigenic extract treated (+ lanes) or not treated (− lanes) with a protease.
FIG. 12 shows the analysis of the antigen of the NP40 extract from human epidermis by electrophoresis under native conditions, where lanes 1–4 and 8–9 contain sera from patients with rheumatoid arthritis and lanes 5–7 contain control sera.
FIG. 13 shows the analysis of proteins in the NP40 extract of mammary epidermis, where immunodetection was carried out with sera from patients with rheumatoid arthritis (lanes 5–12) and control sera (lanes 1–4).

FIG. 11 shows the immunotransfer analysis of the above NP40 antigenic extract, treated or not treated with a nuclease (FIG. 11A) or a protease (FIG. 11B). In (1), the NP40 extract of mammary epidermis was precipitated with TCA, taken up in Tris-CaCl$_2$ buffer and then treated with (+) or without (−) micrococcal nuclease (100 U/ml) for 30 minutes at 37° C. In (FIG. 11B), an NP40 extract of human epidermis identical to the above was precipitated with TCA, then taken up in 1% SDS and treated without (−) or with (+) 10 mg/ml of proteinase K for 30 minutes at 37° C. In all cases, the proteins were separated in SDS-PAGE (8–25%), transferred and then immunodetected with control sera (a) and sera of patients suffering from RA (b) diluted to ¹⁄₁₀₀. The disappearance of the immuno-reactive region after treatment of the extract with proteinase K confirms the protein nature of the molecule carrying the epitope or epitopes recognized by the autoantibodies, whereas this region was not modified after digestion of nucleic acids with micrococcal nuclease.

FIG. 12 shows the analysis of the antigen by electrophoresis under native conditions; this analysis consisted in precipitating the NP40 extract of human epidermis with ethanol, then in performing an immunodetection after PAGE under native conditions (8–25%) and transfer onto nitrocellulose with sera of patients suffering from RA (lanes 1–4 and 8–9) and control sera (lanes 5–7), diluted to ¹⁄₁₀₀. The human antigen separates into several antigenic proteins whose migration is similar to that of reference standards whose molecular weights are between 80 and 400 kD, the most immuno-reactive proteins being located in the regions lying between 80 and 120 kD.

FIG. 13 shows the analysis of the antigen by IEF. The proteins in the NP40 extract of mammary epidermis were precipitated with ethanol, separated by IEF (pHi 3 to 9), transferred onto nitrocellulose and then immunodetected with sera of patients suffering from RA (lanes 5–12) and control sera (lanes 1–4) diluted to ¹⁄₁₀₀. The human antigen exhibits a very heterogeneous distribution of pHi values, the latter varying from 5.8 to 7.4. This heterogeneity of pHi was verified in two-dimensional (IEF/SDS-PAGE) electrophoresis. The protein recognized specifically by the sera of patients suffering from RA, after transfer of such a gel, shows a characteristic "comma"-shaped picture, the apparent molecular weight decreasing proportionately as the pHi becomes more basic.

FIG. 14 shows the analysis of the antigen in two-dimensional IEF/SDS-PAGE gel; the proteins in the NP40 extract of mammary epidermis were precipitated with ethanol, separated by IEF (pHi 5 to 8) followed by SDS-PAGE (12.5%), transferred onto nitrocellulose and immunodetected with a serum of a patient suffering from RA and a control serum.

The marked heterogeneity of the antigen, with respect to both mass and pHi, probably indicates the presence of modified isoforms; it suggests that it could be glycosylated and/or phosphorylated. However, treatment with peptide N-glycosidase F did not modify either its migration or its immunoreactivity after SDS-PAGE.

B—WATER-SOLUBILITY OF THE ANTIGEN 5 cm$^2$ of mammary epidermis were ground mechanically in buffer A or in buffer B. The homogenates were thereafter centrifuged for 10 minutes at 10,000 g and an equal quantity of the soluble proteins in the two supernatants was precipitated with ethanol, then separated by PAGE under native conditions (8–25%), transferred onto nitro-cellulose and then immunodetected with sera of patients suffering from RA and control sera. This study indicates that the antigen is extracted not only in the presence of a detergent (buffer A) but also in its absence (buffer B). In addition, the antigen is always to be found predominantly in the soluble fractions and is present in the pellets in very small amounts. These results indicate that the human antigen, like that of rat esophagus, is a very water-soluble molecule.

C—EXPRESSION OF THE ANTIGEN IN DIFFERENT ANATOMICAL AREAS OF THE EPIDERMIS

Immunotransfer analysis of the proteins in an NP40 extract of abdominal epidermis and of preputial epidermis indicates that the antigen associated with RA is present in the human epidermis irrespective of the sex and anatomical area (breast, abdomen or prepuce) and also of age (children and adults). Since the antigen is histologically localized in the stratum corneum, there is justification for the view that its abundance will depend on the thickness of the latter, which varies according to the anatomical area.

D—IDENTIFICATION OF THE ANTIGEN

The antigen recognized by the sera of patients suffering from RA is not a human epidermal cytokeratin.

FIG. 15 shows:

in (a): an NP40 extract of mammary epidermis immunodetected, after SDS-PAGE (8–25%) and transfer onto nitrocellulose, with a serum of a patient suffering from RA, preincubated on the one hand with the extraction buffer (lane 1), with the extract itself (lane 2) and with an insoluble fraction enriched with respect to epidermal cytokeratins (lane 3).

in (b): the urea-soluble cytokeratins immunodetected, after SDS-PAGE (8–25%) and transfer, with the anticytokeratin MAb F12-19, preincubated either with the extraction buffer (lane 1), or with the epidermal extract (lane 2), or with a fraction enriched with respect to cytokeratins (lane 3), or with the ureasoluble cytokeratins (lane 4).

in (c): the proteins in the epidermal extract (lane 5), in the fraction enriched with respect to cytokeratins (lane 6) and the pure urea-soluble cytokeratins (lane 7) separated by SDS-PAGE (8–25%), transferred and immunodetected with the anticytokeratin MAb F12-19.

The immunoreactivity of the sera of patients suffering from RA has not been inhibited by preincubation of the latter with epidermal cytokeratins (enriched or purified), whereas it has disappeared in the presence of water-soluble extract of skin. Similarly, the monoclonal antibody F12-19 has not recognized in immunotransfer any protein of the antigenic extract.

The characteristic "comma" shape of the antigen in two-dimensional gel and its apparent molecular weight in SDS-PAGE are similar to those of filaggrin, a protein which appears in the stratum granulosum during epidermal differentiation (SARRET et al., Path. Biol. 37:297–303, 1989). The Inventors hence sought to determine whether filaggrin and the antigen of the invention were identical, and whether the sera of patients suffering from RA contained antifilaggrin autoantibodies.

Figure 16D:
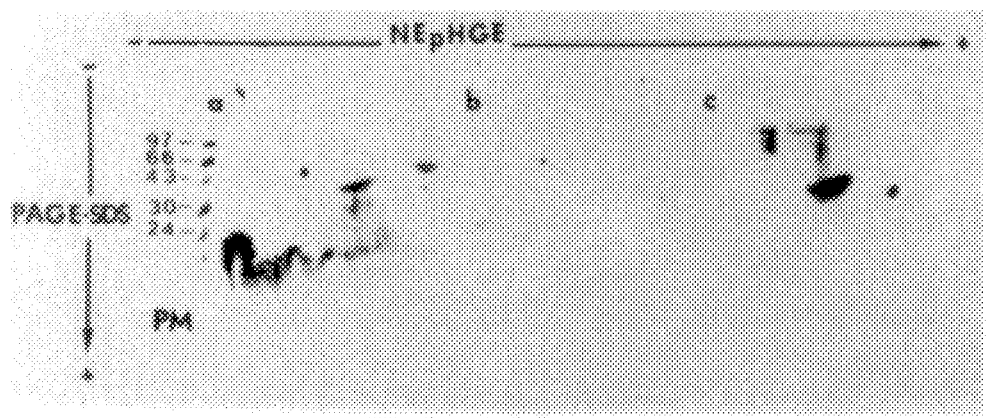
FIG. 16D shows the proteins from FIGS. 16A–C separated by NEPHGE followed by SDS-PAGE, and stained with Ponceau red (panel a), immunodetected with the antifilaggrin MAb AKH-1 (panel b), and immunodetected with serum from a patient with rheumatoid arthritis (panel c).

FIG. 16 shows the analysis of an immunotransfer of the proteins in an extract of mammary epidermis, separated in (A) by SDS-PAGE (12.5%), in (B) by PAGE under native conditions and in (C) by IEF (pHi 3 to 9), then transferred onto nitrocellulose and immunodetected with sera of patients suffering from RA (lanes 1, 3, 6, 7 and 8), the antifilaggrin MAb AKH-1 (lane 2), a control MAb (lane 4) and a control serum (lane 5). These proteins were separated in triplicate (D) by NEpHGE (non-equilibrium pH gradient gel electrophoresis) followed by SDS-PAGE (8–25%), then transferred onto nitrocellulose and stained with Ponceau red (a), or immunodetected with the monoclonal antibody AKH-1 (b), and with a serum of a patient suffering from RA (c). The antigen is recognizable by its characteristic "comma" shape.

The anti-human filaggrin monoclonal antibody AKH-1 recognizes specifically in immunotransfer a human epidermal protein which is soluble in the presence of NP40, possessing the same migration characteristics under conditions of denaturing or native electrophoresis as the RA antigen. After IEF and two-dimensional gel, the antigen and the protein recognized in immunotransfer by AKH-1 present an identical picture.

The Inventors then sought to determine whether the monoclonal antibody AKH-1 could immunoprecipitate the antigen from the epidermal extract in NP40.

Figure 17A:
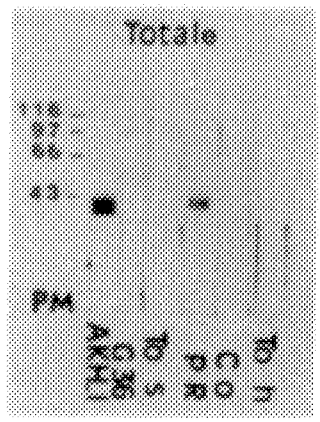
FIG. 17A is the analysis of the proteins in an NP40epidermal extract separated by SDS PAGE before immuno-precipitation with MAb AKH-1, where immunodetection was carried out with serum from a patient with rheumatoid arthritis (RA), control serum ($C_o$), anti-mouse Ig antibodies ($C_o$ m) and anti-human Ig antibodies($C_o$ h).
Figure 17B:
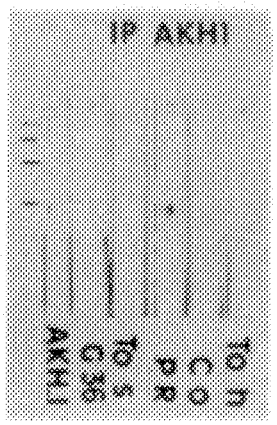
FIG. 17B is the analysis of the proteins in an NP40epidermal extract separated by SDS PAGE after immuno-precipitated with MAb AKH-1, where immunodetection was carried out with serum from a patient with rheumatoid arthritis (RA), control serum ($C_o$), anti-mouse Ig antibodies ($C_o$ m) and anti-human Ig antibodies ($C_o$ h).
Figure 17C:
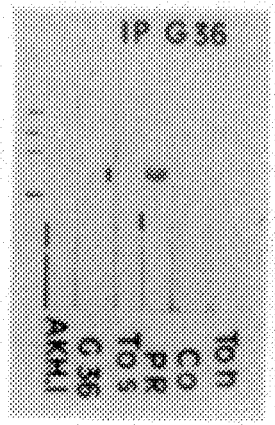
FIG. 17C is the analysis of proteins in an NP40 epidermal extract separated by SDS PAGE after immuno-precipitated with control MAb G36, where immunodetection was carried out with serum from a patient with rheumatoid arthritis (RA), control serum ($C_o$), anti-mouse Ig antibodies ($C_o$ m) and anti-human Ig antibodies ($C_o$ h).
Figure 17D:
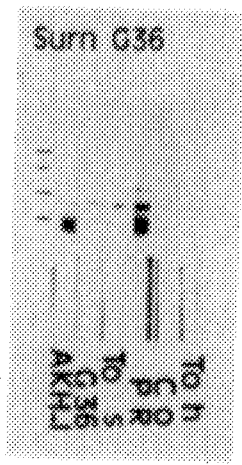
FIG. 17D shows proteins present in the supernatants of fractions immunoprecipitated with MAb G36, above, with immunodetection carried out with serum from a patient with rheumatoid arthritis (RA), control serum ($C_o$), anti-mouse Ig antibodies ($C_o$ m) and anti-human Ig antibodies ($C_o$ h).
Figure 17E:
FIG. 17E shows proteins present in the supernatants of fractions immunoprecipitated with MAb AKH-1, above, with immunodetection carried out with serum from a patient with rheumatoid arthritis (RA), control serum ($C_o$), anti-mouse Ig antibodies ($C_o$ m) and anti-human Ig antibodies ($C_o$ h)

FIGS. 17A–E presents the comparative analysis of the proteins in an NP40 epidermal extract preadsorbed on Protein A-Sepharose, the proteins being separated by SDS-PAGE (12.5%) before immunoprecipitation with the MAb AKH-1 (designated "Total" in FIG. 17A), or after immunoprecipitation with the MAb AKH-1 (designated "IP AKH-1" in FIG. 17B), or with the control MAb G36 (designated "IP G36" in FIG. 17C). After transfer onto nitrocellulose, these proteins were immunodetected with the antibodies AKH-1 and G36, a serum of a patient suffering from RA (RA), a control serum (CO), or with only the anti-mouse Ig ($C_0$ m) and anti-human Ig ($C_0$ h) secondary antibodies. The proteins present in the supernatants of the fractions immunoprecipitated with G36 (designated "Surn G36" in FIG. 17D) and AKH-1 (designated "Surn AKH-1" in FIG. 17E) were analyzed in the same manner after precipitation with TCA.

These results show that AKH-1 has indeed immunoprecipitated an epidermal protein of the same molecular weight as the RA antigen, this molecule being, moreover, recognized specifically in immunotransfer by the sera of patients suffering from RA. This immunoprecipitation was carried out in the presence of 1M NaCl, which makes a co-immunoprecipitation due to a combination between the two proteins (filaggrin and antigen) unlikely. In order to verify that the proteins in the extract recognized by AKH-1 and by the sera of a patient suffering from RA were the same, the supernatants of an immunoprecipitation with the antifilaggrin MAb were subsequently analyzed by immunotransfer with a serum of a patient suffering from RA. FIG. 17 shows that the extract has been exhausted (partially or totally) with respect to the antigen and to filaggrin by the antifilaggrin MAb. Conversely, the sera of patients suffering from RA have not immunoprecipitated the antigen. This negative result may be due to a low affinity of the autoantibodies of the antigen, to an excessively small amount of autoantibodies in the serum or to a failure of these antibodies to recognize the antigen in its native form. The latter hypothesis is unlikely, since the antigen is immunodetectable on nitrocellulose after electrophoresis under native conditions.

Figure 18:
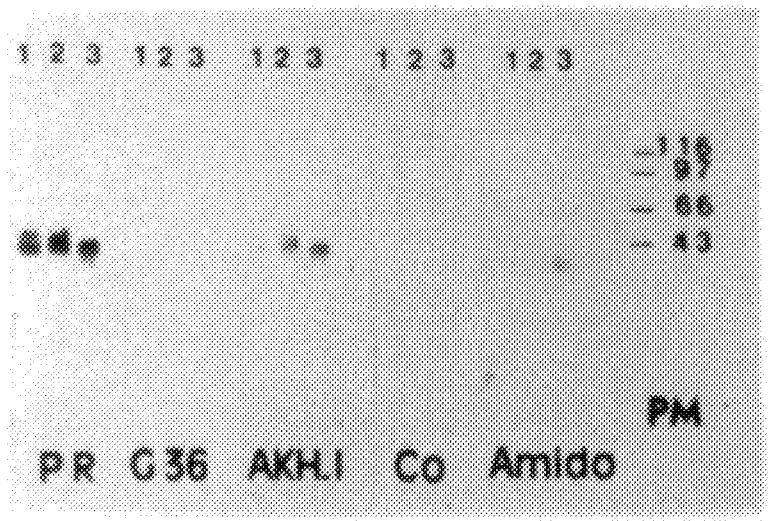
FIG. 18 shows the SDS-PAGE and immunotransfer analysis of the proteins in the various fractions during purification. The total proteins in an extract of human epidermis (lane 1), the soluble proteins after precipitation of the extract with TCA (lane 2) and those in the final purified antigenic fraction (lane 3) were separated by SDS-PAGE (12.5%), transferred onto nitrocellulose and stained with amido black (Amido), or immunodetected with a serum of a patient suffering from RA (RA), a control serum (CO), an antifilaggrin Mab (AKH-1) and a control Mab (G36).

In order to confirm that filaggrin and the RA antigen have at least the epitope detected by the MAb AKH-1 in common, the antigen was purified by elution from a transfer membrane. FIG. 18 shows the SDS-PAGK and immunotransfer analysis of the proteins in the various fractions during the purification. The total proteins in an extract of human epidermis (lane 1), the soluble proteins after precipitation of the extract with TCA (lane 2) and those in the final purified antigenic fraction (lane 3) were separated by SDS-PAGE (12.5%), transferred onto nitrocellulose and stained with amido black (Amido), or immunodetected with a serum of a patient suffering from RA (RA), a control serum (CO), an antifilaggrin MAb (AKH-1) and a control MAb (G36).

The major proteins, which are soluble after precipitation with TCA, appear in the form of a doublet of apparent molecular weight (MW) approximately 40 kD. This doublet is the main immunoreactive band recognized by a serum of a patient suffering from RA. This protein was then purified from a preparative SDS-PAGE gel by transfer and then elution. The RA antigen was specifically immunodetected after SDS-PAGE by the antifilaggrin MAb AKH-1.

Figure 19:
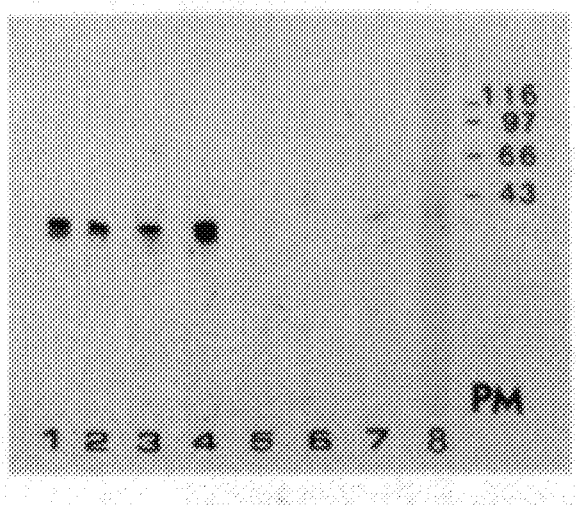
FIG. 19 shows the analysis of purified human filaggrin, analyzed by SDS-PAGE (12.5%), transferred onto nitrocellulose and immunodetected with sera of patients suffering from RA (lanes 1–4), a control serum (lane 5), a control Mab (lane 6) and the Mab AKH-1 (lane 7), or stained with Ponceau red (lane 8).

In order to verify that the sera of patients suffering from RA also recognized human filaggrin, and hence that the latter was closely related to the antigen, the Inventors purified filaggrin according to the method described by LINLEY and DALE (BRA 744:28–35, 1983). FIG. 19 shows the analysis of purified human filaggrin, analyzed by SDS-PAGE (12.5%), transferred onto nitro-cellulose and immunodetected with sera of patients suffering from RA (lanes 1–4), a control serum (lane 5), a control MAb (lane 6) and the MAb AKH-1 (lane 7), or stained with Ponceau red (lane 8). FIG. 19 shows that the sera of patients suffering from RA specifically recognize human filaggrin.

We claim:

1. Method for the in vitro diagnosis of rheumatoid arthritis comprising the steps of:
    (a) contacting a biological sample with at least one antigen selected from the group consisting of:
        i) An antigen extracted from rat esophageal epithelium having a molecular weight of approximately 210 kD and pI values from approximately 5.85 to 6.85;
        ii) An antigen extracted from rat esophageal epithelium having a molecular weight of between 90 and 130 kD and pI values from approximately 5.85 to 7.35;
        iii) An antigen extracted from rat esophageal epithelium having a molecular weight of between 67 and 120 kD and pI values from approximately 5 to 7.5; and
        iv) an antigen extracted from human epidermis having a molecular weight of approximately 40 kD and pI values from approximately 5.8 to 7.4;
    so that the antigen forms an immunological complex with autoantibodies which is specific for rheumatoid arthritis which may be present in said biological sample; and
    (b) detecting the presence of the immunological complex in said biological sample, wherein the presence of the complex is an indicator of rheumatoid arthritis.

2. Kit for the in vitro diagnosis of rheumatoid arthritis from a biological sample, comprising:
    (a) at least one antigen selected from the group consisting of:
        i) An antigen extracted from rat esophageal epithelium having a molecular weight of approximately 210 kD and pI values from approximately 5.85 to 6.85;
        ii) An antigen extracted from rat esophageal epithelium having a molecular weight of between 90 and 130 kD and pI values from approximately 5.85 to 7.35;
        iii) An antigen extracted from rat esophageal epithelium having a molecular weight of between 67 and 120 kD and pI values from approximately 5 to 7.5; and
        iv) an antigen extracted from human epidermis having a molecular weight of approximately 40 kD and pI values from approximately 5.8 to 7.4;
    (b) reagents for preparing a medium for an immunological reaction; and
    (c) at least one reagent capable of detecting an immunological complex wherein the presence of the complex is an indicator of rheumatoid arthritis.

* * * * *